(12) United States Patent
Jinks et al.

(10) Patent No.: US 8,616,201 B2
(45) Date of Patent: *Dec. 31, 2013

(54) MEDICINAL INHALATION DEVICES AND COMPONENTS THEREOF

(75) Inventors: Philip A. Jinks, Loughborough (GB); Rudolf J. Dams, Antwerp (BE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/741,497

(22) PCT Filed: Nov. 6, 2008

(86) PCT No.: PCT/US2008/082608
§ 371 (c)(1),
(2), (4) Date: May 5, 2010

(87) PCT Pub. No.: WO2009/061902
PCT Pub. Date: May 14, 2009

(65) Prior Publication Data
US 2010/0263667 A1    Oct. 21, 2010

(30) Foreign Application Priority Data

Nov. 6, 2007 (GB) .................................. 0721737.5

(51) Int. Cl.
*A61M 15/00* (2006.01)
*B05D 1/00* (2006.01)

(52) U.S. Cl.
USPC .................. 128/203.15; 128/203.12; 427/2.1; 427/387; 428/336; 428/447; 428/450; 428/451

(58) Field of Classification Search
USPC .................. 128/203.12, 203.15; 427/2.1, 387; 428/336, 447, 450, 451
See application file for complete search history.

(56) References Cited

U.S. PATENT DOCUMENTS

| | | |
|---|---|---|
| 3,810,874 A | 5/1974 | Mitsch |
| 4,991,822 A | 2/1991 | Enke |
| 5,772,085 A | 6/1998 | Bryant et al. |
| 6,228,471 B1 | 5/2001 | Neerinck et al. |
| 6,405,934 B1 | 6/2002 | Hess et al. |
| 6,596,260 B1 | 7/2003 | Brugger et al. |
| 6,630,205 B2 * | 10/2003 | Brueck et al. ................. 427/387 |
| 6,649,272 B2 | 11/2003 | Moore et al. ................. 428/447 |
| 6,696,157 B1 | 2/2004 | David et al. |
| 6,878,419 B2 | 4/2005 | David et al. |
| 7,094,471 B2 * | 8/2006 | Moore et al. ................. 428/447 |
| 7,097,910 B2 | 8/2006 | Moore et al. ................. 428/447 |

(Continued)

FOREIGN PATENT DOCUMENTS

| | | |
|---|---|---|
| WO | WO 96/32099 | 10/1996 |
| WO | WO 96/32150 | 10/1996 |

(Continued)

OTHER PUBLICATIONS

International Search Report for PCT/US2008/082593 prepared by the Korean Intellectual Property Office, May 15, 2009.

(Continued)

*Primary Examiner* — D. S. Nakarani

(57) ABSTRACT

A medicinal inhalation device having applied to a surface thereof a composition comprising a multifunctional polyfluoropolyether silane.

14 Claims, 4 Drawing Sheets

(56) References Cited

U.S. PATENT DOCUMENTS

| | | | |
|---|---|---|---|
| 2003/0031806 A1 | 2/2003 | Jinks | |
| 2003/0089368 A1 | 5/2003 | Zhao | |
| 2003/0103906 A1 | 6/2003 | Ashurst et al. | |
| 2003/0138559 A1 | 7/2003 | Ashurst et al. | |
| 2003/0148030 A1 | 8/2003 | Vernon, Jr. et al. | |
| 2003/0183223 A1 | 10/2003 | Hailey et al. | |
| 2003/0187496 A1 | 10/2003 | Kirk et al. | |
| 2004/0092675 A1 | 5/2004 | Moore et al. | 525/533 |
| 2004/0223916 A1 | 11/2004 | Burt et al. | |
| 2005/0061705 A1 | 3/2005 | Spallek et al. | |
| 2005/0133025 A1 | 6/2005 | Laiho et al. | |
| 2010/0242958 A1* | 9/2010 | Jinks et al. | 128/203.12 |
| 2012/0097159 A1* | 4/2012 | Iyer et al. | 128/203.12 |
| 2012/0103330 A1 | 5/2012 | David et al. | 128/203 |

FOREIGN PATENT DOCUMENTS

| | | |
|---|---|---|
| WO | WO 96/32151 | 10/1996 |
| WO | WO 96/32345 | 10/1996 |
| WO | WO 99/00315 | 1/1999 |
| WO | WO 99/42154 | 8/1999 |
| WO | WO 01/64273 | 9/2001 |
| WO | WO 01/64274 | 9/2001 |
| WO | WO 01/64275 | 9/2001 |
| WO | WO 01/64524 | 9/2001 |
| WO | WO 02/30498 | 4/2002 |
| WO | WO 02/47829 | 6/2002 |
| WO | WO 02/100928 | 12/2002 |
| WO | WO 03/006181 | 1/2003 |
| WO | WO 03/024623 | 3/2003 |
| WO | WO 2004/022142 | 3/2004 |
| WO | WO 2008/051789 | 5/2008 |

OTHER PUBLICATIONS

International Search Report for PCT/US2008/082600 prepared by the Korean Intellectual Property Office, May 22, 2009.

International Search Report for PCT/US2008/082608 prepared by the Korean Intellectual Property Office, May 22, 2009.

International Search Report for PCT/US2008/082614 prepared by the Korean Intellectual Property Office, Jun. 8, 2009.

* cited by examiner

MEDICINAL INHALATION DEVICES AND COMPONENTS THEREOF

CROSS REFERENCE TO RELATED APPLICATIONS

This application is a national stage filing under 35 U.S.C. 371 of PCT/US2008/082608, filed Nov. 6, 2008, which claims priority to Great Britain Application No. 0721737.5, filed Nov. 6, 2007, the disclosure of which is incorporated by reference in its/their entirety herein.

FIELD OF THE INVENTION

The present invention relates to medicinal inhalation devices and components for such devices as well as methods of making such devices and components.

BACKGROUND OF THE INVENTION

Medicinal inhalation devices, including pressurized inhalers, such as metered dose pressurized inhalers (MDIs), and dry powder inhalers (DPIs), are widely used for delivering medicaments.

Medicinal inhalation devices typically comprise a plurality of hardware components, (which in the case of a MDI can include gasket seals; metered dose valves (including their individual components, such as ferrules, valve bodies, valve stems, tanks, springs retaining cups and seals); containers; and actuators) as well as a number of internal surfaces which may be in contact with the medicinal formulation during storage or come in contact with the medicinal formulation during delivery. Often a desirable material for a particular component is found to be unsuitable in regard to its surface properties, e.g. surface energy, and/or its interaction with the medicinal formulation. For example, the relatively high surface energy of materials typically used in MDIs, e.g. acetal polymer for valve stems, or deep drawn stainless steels or aluminum for containers, can cause medicament particles in suspension formulations to adhere irreversibly to the surfaces of corresponding component(s), which has a consequent impact on the uniformity of medicinal delivery. Similar effects are also observed for DPIs. Other examples of potentially undesirable interactions between a component and the medicinal formulation may include enhanced medicament degradation; adsorption of medicament or permeation of a formulation constituent or extraction of chemicals from plastic materials. For DPIs often permeation and adsorption of ambient water pose issues. Also the use of materials having relatively high surface energy for certain components (e.g. metered dose valves and/or individual components thereof), may have undesirable effects for the operation of movable components of a medicinal inhalation device.

Various coatings have been proposed for particular components or surfaces of metered dose inhalers, see e.g. EP 642 992, WO 96/32099, WO 96/32150-1, WO 96/32345, WO 99/42154, WO 02/47829, WO03/024623; WO 02/30498, WO 01/64273; WO 91/64274-5; WO 01/64524; and WO 03/006181.

SUMMARY OF THE INVENTION

Although a number of different coatings have been proposed, there is an ongoing need for medicinal inhalation devices and components thereof having desirable surface properties (e.g. low surface energy) in conjunction with desirable structural integrity (e.g. adhesion, durability, robustness and/or resistance to degradation over the lifetime of the device) of a coating system provided on said devices and components as well as methods of providing such medicinal inhalation devices and components.

In aspects of the present invention there is provided a method of making a medicinal inhalation device or a component of a medicinal inhalation device comprising a step of: applying to at least a portion of a surface of the device or the component, respectively, a composition comprising a multifunctional polyfluoropolyether silane.

It has been found that the use of a multifunctional polyfluoropolyether silane (in particular a difunctional polyfluoropolyether silane) allows for high application efficiency and coverage as well as extensive bonding (e.g. covalent bonding) to said surface and cross-linking within the polyfluoropolyether-containing coating itself, to provide very desirable structural integrity of applied polyfluoropolyether-containing coating.

The term "multifunctional polyfluoropolyether silane" as used herein is generally understood to mean a multivalent polyfluoropolyether segment functionalized with a multiple of functional silane groups, and the term "difunctional polyfluoropolyether silane" as used herein is generally understood to mean a divalent polyfluoropolyether segment functionalized with a multiple of functional silane groups (in particular two to four functional silane groups, more particularly two functional silane groups).

For enhanced stability and/or resistance to attack (e.g. by ethanol, medicament, and/or other potential components of medicinal inhalation formulations) desirably the polyfluoropolyether segment is not linked to silane groups via a functionality that includes a nitrogen-silicon bond or a sulfur-silicon bond. In particular, for enhanced stability and resistance of the applied polyfluoropolyether-containing coating to attack, it is desirable that polyfluoropolyether segment is linked to silane groups via a functionality that includes a carbon-silicon bond, more particularly via a —$C(R)_2$—Si functionality where R is independently hydrogen or a $C_{1-4}$ alkyl group (preferably R is hydrogen), and most particularly, via a —$(C(R)_2)_k$—$C(R)_2$—Si functionality where k is at least 2 (preferably 2 to about 25, more preferably 2 to about 15, most preferably 2 to about 10) and again where R is independently hydrogen or a $C_{1-4}$ alkyl group (preferably R is hydrogen). The inclusion of —$(C(R)_2)_k$— where k is at least 2 advantageously, additionally provides flexural strength.

For enhanced surface properties as well as coating efficiency, preferably the polyfluoropolyether segment is a perfluorinated polyfluoropolyether segment. The use of polyfluoropolyether segments including perfluorinated repeating units including short chains of carbon, where desirably the number of carbon atoms in sequence is at most 6, more desirably at most 4, even more desirably at most 3, and most desirably at most 2, additionally facilitating durability/flexibility of the applied polyfluoropolyether-containing coating as well as minimizing a potential of bioaccumulation of perfluorinated moieties.

For certain embodiments, the weight average molecular weight of the polyfluoropolyether segment is about 1000 or higher, more desirably about 1800 or higher. Higher weight average molecular weights further facilitate durability as well as minimizing a potential of bioaccumulation. Generally for ease in use and application, the weight average molecular weight of the polyfluoropolyether segment is desirably about 6000 at most and more desirably about 4000 at most.

The application of compositions comprising multifunctional polyfluoropolyether silanes as described herein is also advantageous in that said application allows the provision of very thin polyfluoropolyether-containing coatings—yet having desirable surface properties together with advantageous structural integrity. Preferably the thickness is at most about 300 nm, more preferably at most about 200 nm, even more preferably at most about 150 nm, and most preferably at most about 100 nm. For certain of these embodiments, the thickness of the polyfluoropolyether-containing coating is at least about 20 nm, preferably at least about 30 nm, and most preferably at least about 50 nm.

Additional aspects of the present invention include: devices and components made in accordance with aforesaid methods.

Other aspects of the present invention include a medicinal inhalation device or a component of a medicinal inhalation device comprising a polyfluoropolyether-containing coating bonded to at least a portion of a surface of the device or the component, respectively, said polyfluoropolyether-containing coating comprising a plurality of cross-linked, multifunctional polyfluoropolyether silane entities and said polyfluoropolyether-containing coating sharing at least one covalent bond with said surface.

Dependent claims define further embodiments of the invention

The invention, in its various combinations, either in method or apparatus form, may also be characterized by the following listing of items:

1. A method of making a medicinal inhalation device comprising a step of: applying to at least a portion of a surface of the device a composition comprising a multifunctional polyfluoropolyether silane.
2. A method of making a component of a medicinal inhalation device comprising a step of: applying to at least a portion of a surface of the component a composition comprising a multifunctional polyfluoropolyether silane.
3. A method according to item 1 or item 2, wherein the polyfluoropolyether segment of the polyfluoropolyether silane is not linked to the functional silane groups via a functionality that includes nitrogen-silicon bond or a sulfur-silicon bond.
4. A method according to any one of items 1 to 3, wherein the polyfluoropolyether segment of the polyfluoropolyether silane is linked to the functional silane groups via a functionality that includes a carbon-silicon bond.
5. A method according to item 4, wherein the polyfluoropolyether segment of the polyfluoropolyether silane is linked to the functional silane groups via a —C(R)$_2$—Si functionality where R is independently hydrogen or a C$_{1-4}$ alkyl group.
6. A method according to item 5, wherein the polyfluoropolyether segment of the polyfluoropolyether silane is linked to the functional silane groups via a —(CR$_2$)$_k$—C(R)$_2$—Si functionality where k is at least 2 and where R is independently hydrogen or a C$_{1-4}$ alkyl group.
7. A method according to any one of items 1 to 6, wherein the functional silane group comprises at least one hydrolysable group.
8. A method according to item 7, wherein the functional silane group comprises at least two hydrolysable groups, more particularly three hydrolysable groups.
9. A method according to any one of items 1 to 8, wherein the polyfluoropolyether segment of the polyfluoropolyether is a perfluorinated polyfluoropolyether segment.
10. A method according to item 9, wherein in the repeating units of the perfluorinated polyfluoropolyether segment the number of carbon atoms in sequence is at most 6.
11. A method according to item 10, wherein in the repeating units of the perfluorinated polyfluoropolyether segment the number of carbon atoms in sequence is at most 4, more particularly at most 3, and most particularly at most 2.
12. A method according to any one of the preceding items, wherein the multifunctional polyfluoropolyether silane is a difunctional polyfluoropolyether silane.
13. A method according to any one of items 1 to 5, wherein the polyfluoropolyether silane is of Formula Ia:

wherein:
  R$_f$ is a multivalent polyfluoropolyether segment;
  Q is an organic divalent or trivalent linking group;
  each R is independently hydrogen or a C$_{1-4}$ alkyl group;
  each Y is independently a hydrolysable group;
  R$^{1a}$ is a C$_{1-8}$ alkyl or phenyl group;
  x is 0 or 1 or 2;
  y is 1 or 2; and
  z is 2, 3, or 4.

14. A method according to item 13, wherein the polyfluoropolyether segment, R$_f$, comprises perfluorinated repeating units selected from the group consisting of —(C$_n$F$_{2n}$O)—, (CF(Z)O)—, —(CF(Z)C$_n$F$_{2n}$O)—, —(C$_n$F$_{2n}$CF(Z)O)—, —(CF$_2$CF(Z)O)—, and combinations thereof; wherein n is an integer from 1 to 6 and Z is a perfluoroalkyl group, an oxygen-containing perfluoroalkyl group, a perfluoroalkoxy group, or an oxygen-substituted perfluoroalkoxy group, each of which can be linear, branched, or cyclic, and have 1 to 5 carbon atoms and up to 4 oxygen atoms when oxygen-containing or oxygen-substituted and wherein for repeating units including Z the number of carbon atoms in sequence is at most 6.
15. A method according to item 14, wherein n is an integer from 1 to 4 and wherein for repeating units including Z the number of carbon atoms in sequence is at most four.
16. A method according to item 14 or item 15, wherein n is an integer from 1 to 3 and wherein for repeating units including Z the number of carbon atoms in sequence is at most three.
17. A method according to any one of items 13 to 16, wherein the polyfluoropolyether segment, R$_f$, comprises perfluorinated repeating units selected from the group consisting of —(C$_n$F$_{2n}$O)—, —(CF(Z)O)—, and combinations thereof; wherein n is 1 or 2 and Z is an —CF$_3$ group.
18. A method according to any one of items 13 to 17, wherein the polyfluoropolyether segment, R$_f$, is divalent and z is 2.
19. A method according to any one of items 13 to 15, wherein z is 2, and R$_f$ is selected from the group consisting of —CF$_2$O(CF$_2$O)$_m$(C$_2$F$_4$O)$_p$CF$_2$—, —CF(CF$_3$)O(CF(CF$_3$)CF$_2$O)$_p$CF(CF$_3$)—, —CF$_2$O(C$_2$F$_4$O)$_p$CF$_2$—, —(CF$_2$)$_3$O(C$_4$F$_8$O)$_p$(CF$_2$)$_3$—, —CF(CF$_3$)—(OCF$_2$CF(CF$_3$))$_p$O—C$_t$F$_{2t}$—O(CF(CF$_3$)CF$_2$O)$_p$CF(CF$_3$)—, wherein t is 2, 3 or 4 and wherein m is 1 to 50, and p is 3 to 40.
20. A method according to item 19, wherein R$_f$ is selected from the group consisting of —CF$_2$O(CF$_2$O)$_m$(C$_2$F$_4$O)$_p$CF$_2$—, —CF$_2$O(C$_2$F$_4$O)$_p$CF$_2$—, and —CF(CF$_3$)—(OCF$_2$CF(CF$_3$))$_p$O—(C$_t$F$_{2t}$)—O(CF(CF$_3$)CF$_2$O)$_p$CF(CF$_3$)—, and wherein t is 2, 3, or 4, and wherein the average value of m+p or p+p or p is from about 4 to about 24.
21. A method according to any one of items 13 to 20, wherein Q is selected from the group consisting of —C(O)N(R)—(CH$_2$)$_k$—, —S(O)$_2$N(R)—(CH$_2$)$_k$—, —(CH$_2$)$_k$—, —CH$_2$O—(CH$_2$)$_k$—, —C(O)S—(CH$_2$)$_k$—, —CH$_2$OC(O)N(R)—(CH$_2$)$_k$—, and

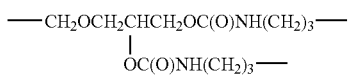

wherein R is hydrogen or $C_{1-4}$ alkyl, and k is 2 to about 25.

22. A method according to item 21, wherein Q is selected from the group consisting of —C(O)N(R)(CH$_2$)$_2$—, —OC(O)N(R)(CH$_2$)$_2$—, —CH$_2$—O—(CH$_2$)$_2$—, or —CH$_2$—OC(O)N(R)—(CH$_2$)$_2$—, wherein R is hydrogen or $C_{1-4}$ alkyl and y is 1.

23. A method according to any one of items 13 to 22, wherein x is 0.

24. A method according to item 5 or item 6 or any one of items 13 to 23, wherein R is hydrogen.

25. A method according to item 7 or item 8 or any one of items 13 to 23 or item 24 as dependent on any one of items 13 to 23, wherein each hydrolysable group is independently selected from the group consisting of hydrogen, halogen, alkoxy, acyloxy, polyalkyleneoxy, and aryloxy groups.

26. A method according to item 25, wherein each hydrolysable group is independently selected from the group consisting of alkoxy, acyloxy, aryloxy, and polyalkyleneoxy groups.

27. A method according to item 25 or item 26, wherein each hydrolysable group is independently an alkoxy group, in particular an alkoxy group —OR' wherein each R' is independently a $C_{1-6}$alkyl, in particular a $C_{1-4}$ alkyl.

28. A method according to any one of items 13 to 27, wherein $R_f$ is —CF$_2$O(CF$_2$O)$_m$(C$_2$F$_4$O)$_p$CF$_2$—, and Q-C(R)$_2$—Si(Y')$_{3-x}$(R$^{1a}$)$_x$ is C(O)NH(CH$_2$)$_3$Si(OR')$_3$, wherein R' is methyl or ethyl.

29. A method according to any one of the preceding items, wherein the weight average molecular weight of the polyfluoropolyether segment is about 1000 or higher, in particular about 1800 or higher.

30. A method according to any one of the preceding items, wherein the weight average molecular weight of the polyfluoropolyether segment is about 6000 or less, in particular about 4000 or less.

31. A method according to any one of the preceding items, wherein the amount of polyfluoropolyether silane having a polyfluoropolyether segment having a weight average molecular weight less than 750 is not more than 10% by weight of total amount of polyfluoropolyether silane, in particular not more than 5% by weight of total amount of polyfluoropolyether silane, more particularly not more than 1% by weight of total amount of polyfluoropolyether silane, and most particularly 0% by weight of total amount of polyfluoropolyether silane.

32. A method according to any one the preceding items, wherein the composition further comprises an organic solvent, in particular an organic solvent selected from the group consisting of a fluorinate solvent, a lower alcohol and mixtures thereof.

33. A method according to any one of the preceding items, wherein the composition further comprises an acid.

34. A method according to any one of the preceding items, wherein the composition further comprises water.

35. A method according to any one of the preceding items, wherein the composition further comprises a non-fluorinated cross-linking agent.

36. A method according to item 35, wherein the cross-linking agent comprises one or more non-fluorinated compounds, each compound being independently selected from the group consisting of a non-fluorinated compound having at least two hydrolysable groups and a non-fluorinated compound having at least one reactive functional group and at least one hydrolysable group.

37. A method according to item 36, wherein said non-fluorinated compound having at least two hydrolysable groups has at least three hydrolysable groups, and more particularly said compound has four hydrolysable groups and/or said non-fluorinated compound having at least one reactive functional group and at least one hydrolysable group has at least two hydrolysable groups, and more particularly said compound has three hydrolysable groups.

38. A method according to item 35 or 36, wherein the cross-linking agent comprises a non-fluorinated compound of silicon selected from the group consisting of a non-fluorinated silicon compound of Formula IIa, a non-fluorinated silicon compound of Formula IIIa and a mixture of a non-fluorinated silicon compound of Formula IIa and a non-fluorinated silicon compound of Formula IIa, where a compound of Formula IIa is a non-fluorinated silicon compound in accordance to the following Formula IIa:

and a compound of Formula IIIa is a non-fluorinated silicon compound in accordance to the following Formula IIIa:

where L represents a reactive functional group;
Q' represents an organic divalent linking group;
R is independently hydrogen or a $C_{1-4}$ alkyl group; and
where, for Formulas IIa and IIIa,
$R^5$ represents a non-hydrolysable group;
$Y^2$ represents a hydrolysable group; and
g is 0, 1 or 2.

39. A method according to item 38, wherein g is 0 or 1, in particular 0.

40. A method according to item 38 or item 39, wherein each hydrolysable group $Y^2$ is independently an alkoxy group, in particular an alkoxy group —OR$^6$ where each R$^6$ is independently a $C_{1-4}$ alkyl.

41. A method according to any one of items 38 to 40, wherein L represents a reactive functional group selected from the group consisting of an amino group, an epoxy group, a mercaptan group, an anhydride group, vinyl ether group, vinyl ester group, an allyl group, allyl ester group, vinyl ketone group, styrene group, vinyl amide group, acrylamide group, maleate group, fumarate group, acrylate group and methacrylate group.

42. A method according to any one of items 35 to 41, wherein the cross-linking agent comprises a compound selected from group consisting of tetramethoxysilane; tetraethoxysilane; tetrapropoxysilane; tetrabutoxysilane; methyl triethoxysilane; dimethyldiethoxysilane; octadecyltriethoxysilane; 3-glycidoxypropyltrimethoxysilane; 3-glycidoxypropyltriethoxysilane; 3-aminopropyltrimethoxysilane; 3-aminopropyl-his (3-trimethoxysilylpropyl)amine; 3-aminopropyl tri (methoxyethoxyethoxy) silane; N (2-aminoethyl)-3-aminopropyltrimethoxysilane; his (3-trimethoxysilylpropyl) ethylenediamine; 3-mercaptopropyltrimethoxysilane; 3-mercaptopropyltriethoxysilane; 3-trimethoxysilyl-propylmethacrylate; 3-triethoxysilypropylmethacrylate; his (trimethoxysilyl) itaconate; allyltriethoxysilane; allyltrimetoxysilane; 3-"N-allylamino)propyltrimethoxysilane; vinyltrimethoxysilane; vinyltriethoxysilane; and mixtures thereof.

43. A method according to any one of the preceding items, wherein method includes a pre-treatment step prior to the step of applying the composition, said pre-treatment step comprising exposing said surface to a corona discharge or an oxygen plasma.

44. A method according to any one of the preceding items, wherein said surface is aluminum or an aluminum alloy, and wherein the method further comprises a step of anodizing said surface, said step of anodizing being performed prior to the step of applying the composition and in a method according to item 43, said step of anodizing being performed prior to the pre-treatment step.

45. A method according to any one of the preceding items, wherein the method further comprises a step of forming a component of the medicinal inhalation device or the component, respectively, using a oil comprising a hydrofluoroether or a mixture of hydrofluoroethers, said step of forming being performed being prior to the step of applying the composition, and in a method according item 43, said step of forming being performed prior to the pre-treatment step, and in a method according to item 44, said step of forming being performed prior to the step of anodizing.

46. A method according to item 45, wherein the hydrofluoroether is selected from the group consisting of methyl heptafluoropropylether; methyl nonafluorobutylether; ethyl nonafluorobutylether; 2-trifluoromethyl-3-ethoxydodecafluorohexane and mixtures thereof.

47. A method according to item 45 or item 46, wherein the step of forming is deep drawing, machining or impact extruding.

48. A method according to any one of items 35 to 43, wherein said surface is a non-metal surface, in particular a plastic surface.

49. A method according to any one of the preceding items, wherein the composition is applied by spraying, dipping, rolling, brushing, spreading or flow coating, in particular by spraying or dipping.

50. A method according to any one of the preceding items, wherein after applying the composition, the method further comprises a step of curing.

51. A method according to item 50, wherein the curing is carried out at an elevated temperature in the range from about 40° C. to about 300° C.

52. A method according to any one of the preceding items, wherein the composition is applied to said surface, such that polyfluoropolyether-containing coating provided on said surface has a thickness of at most about 300 nm, in particular at most about 200 nm, more particularly at most about 150 nm, and even more particularly at most about 100 nm.

53. A method according to any one of the preceding items, wherein the composition is applied to said surface, such that polyfluoropolyether-containing coating provided on said surface has a thickness of at least about 20 nm, in particular at least about 30 nm, and more particularly at least about 50 nm.

54. A method according to any one of the preceding items, where said surface of the device or said surface of the component of the device, as applicable, is a surface that is or will come in contact with a medicament or a medicinal formulation during storage or delivery from the medicinal inhalation device.

55. A method according to any one of the preceding items, where said surface of the device or said surface of the component of the device, as applicable, is a surface that comes in contact with a movable component of the device or is a surface of a movable component of the device.

56. A method according to any one of the preceding items, wherein the method is free of a step of pre-coating said surface prior to applying the composition.

57. A method according to any one of the preceding items, where said medicinal inhalation device is a metered dose inhaler or a dry powder inhaler.

58. A medicinal inhalation device made according to item 1 or any one of items 3 to 57 as directly or indirectly dependent on item 1.

59. A component of a medical inhalation device made according to item 2 or any one of items 3 to 57 as directly or indirectly dependent on item 2.

60. A medicinal inhalation device comprising a polyfluoropolyether-containing coating bonded to at least a portion of a surface of the device, said polyfluorpolyether-containing coating comprising a plurality of cross-linked, multifunctional polyfluoropolyether-silane entities and said polyfluorpolyether-containing coating sharing at least one covalent bond with said surface.

61. A component of a medicinal inhalation device comprising a polyfluoropolyether-containing coating bonded on at least a portion of a surface of the component, said polyfluorpolyether-containing coating comprising a plurality of cross-linked, multifunctional polyfluoropolyether silane entities and said polyfluorpolyether-containing coating sharing at least one covalent bond with said surface.

62. A device according to item 60 or a component according to item 61, wherein the polyfluoropolyether segment of the polyfluoropolyether silane entities is not linked to the functional silane groups via a functionality that includes nitrogen-silicon bond or a sulfur-silicon bond.

63. A device according to item 60 or item 62 as dependent on item 60 or a component according to item 61 or item 62 as dependent on item 61, wherein the polyfluoropolyether segment of the polyfluoropolyether silane entities is linked to the functional silane groups via a functionality that includes a carbon-silicon bond.

64. A device according to item 63 as directly or indirectly dependent on item 60, or a component according to item 63, as directly or indirectly dependent on item 61, wherein the polyfluoropolyether segment is linked to the functional silane groups via a —$C(R)_2$—Si functionality where R is independently hydrogen or a $C_{1-4}$ alkyl group.

65. A device according to item 64 as directly or indirectly dependent on item 60, or a component according to item 64, as directly or indirectly dependent on item 61, wherein the polyfluoropolyether segment is linked to the functional silane groups via a —$(CR_2)_k$—$C(R)_2$—Si functionality where k is at least 2 and where R is independently hydrogen or a $C_{1-4}$ alkyl group.

66. A device according to item 60 or any one of items 62 to 65 as directly or indirectly dependent on item 60, or a component according to item 61 or any one of items 62 to 65 as directly or indirectly dependent on item 61, wherein the polyfluoropolyether segment of the polyfluoropolyether silane entities is a perfluorinated polyfluoropolyether segment.

67. A device according to item 66 as directly or indirectly dependent on item 60, or a component according to item 66 as directly or indirectly dependent on item 61, wherein in the repeating units of the perfluorinated polyfluoropolyether segment the number of carbon atoms in sequence is at most 6.

68. A device according to item 67 as directly or indirectly dependent on item 60, or a component according to item 67 as directly or indirectly dependent on item 61, wherein the number of carbon atoms in sequence is at most 4, in particular at most 3, and more particularly at most 2.

69. A device according to item 60 or any one of items 62 to 68 as directly or indirectly dependent on item 60, or a component according to item 61 or any one of items 62 to 68 as directly or indirectly dependent on item 61, wherein the at least one covalent bond shared with the surface is a bond in a —O—Si group.

70. A device according to item 60 or any one of items 62 to 69 as directly or indirectly dependent on item 60, or a component according to item 61 or any one of items 62 to 69 as directly or indirectly dependent on item 61, wherein the polyfluoropolyether-containing coating shares a plurality of covalent bonds with the surface.

71. A device according to item 60 or any one of items 62 to 70 as directly or indirectly dependent on item 60, or a component according to item 61 or any one of items 62 to 70 as directly or indirectly dependent on item 61, wherein the multifunctional polyfluoropolyether silane entities include difunctional polyfluoropolyether silane entities.

72. A device according to item 60 or any one of items 62 to 64 as directly or indirectly dependent on item 60, or a component according to item 61 or any one of items 62 to 64 as directly or indirectly dependent on item 61, wherein the polyfluoropolyether-containing coating comprises polyfluoropolyether silane entities of the following Formula Ib:

$$R_f[Q\text{-}[C(R)_2\text{—}Si(O\text{—})_{3-x}(R^{1a})_x]_y]_z \quad \text{Ib}$$

wherein:
R$_f$ is multivalent polyfluoropolyether segment;
Q is an organic divalent or trivalent linking group;
each R is independently hydrogen or a C$_{1-4}$ alkyl group;
R$^{1a}$ is a C$_{1-8}$ alkyl or phenyl group;
x is 0 or 1 or 2;
y is 1 or 2; and
z is 2, 3, or 4.

73. A device according to item 72 as directly or indirectly dependent on item 60, or a component according to item 72 as directly or indirectly dependent on item 61, wherein entities of Formula Ib share at least one covalent bond with said surface and wherein said at least one covalent bond is a bond to an oxygen atom in Si(O—)$_{3-x}$.

74. A device according to item 72 or item 73 as directly or indirectly dependent on item 60, or a component according to item 72 or item 73 as directly or indirectly dependent on item 61, wherein the polyfluoropolyether segment, R$_f$, comprises perfluorinated repeating units selected from the group consisting of —(C$_n$F$_{2n}$O)—, —(CF(Z)O)—, —(CF(Z)C$_n$F$_{2n}$O)—, —(C$_n$F$_{2n}$CF(Z)O)—, —(CF$_2$CF(Z)O)—, and combinations thereof; wherein n is an integer from 1 to 6 and Z is a perfluoroalkyl group, an oxygen-containing perfluoroalkyl group, a perfluoroalkoxy group, or an oxygen-substituted perfluoroalkoxy group, each of which can be linear, branched, or cyclic, and have 1 to 5 carbon atoms and up to 4 oxygen atoms when oxygen-containing or oxygen-substituted and wherein for repeating units including Z the number of carbon atoms in sequence is at most 6.

75. A device according to item 74 as directly or indirectly dependent on item 60, or a component according to item 74 as directly or indirectly dependent on item 61, wherein n is an integer from 1 to 4 and wherein for repeating units including Z the number of carbon atoms in sequence is at most four.

76. A device according to item 74 or item 75 as directly or indirectly dependent on item 60, or a component according to item 74 or item 75 as directly or indirectly dependent on item 61, wherein n is an integer from 1 to 3 and wherein for repeating units including Z the number of carbon atoms in sequence is at most three.

77. A device according to any one of items 72 to 76 as directly or indirectly dependent on item 60, or a component according to any one of items 72 to 76 as directly or indirectly dependent on item 61, wherein the polyfluoropolyether segment, R$_f$, comprises perfluorinated repeating units selected from the group consisting of —(C$_n$F$_{2n}$O)—, —(CF(Z)O)—, and combinations thereof; wherein n is 1 or 2 and Z is an —CF$_3$ group.

78. A device according to any one of items 72 to 77 as directly or indirectly dependent on item 60, or a component according to any one of items 72 to 77 as directly or indirectly dependent on item 61, wherein the polyfluoropolyether segment, R$_f$, is divalent and z is 2.

79. A device according to any one of items 72 to 75 as directly or indirectly dependent on item 60, or a component according to any one of items 72 to 75 as directly or indirectly dependent on item 61, wherein z is 2, and R$_f$ is selected from the group consisting of —CF$_2$O(CF$_2$O)$_m$(C$_2$F$_4$O)$_p$CF$_2$—, —CF(CF$_3$)O(CF(CF$_3$)CF$_2$O)$_p$CF(CF$_3$)—, —CF$_2$O(C$_2$F$_4$O)$_p$CF$_2$—, —(CF$_2$)$_3$O(C$_4$F$_8$O)$_p$(CF$_2$)$_3$—, —CF(CF$_3$)—(OCF$_2$CF(CF$_3$))$_p$O—C$_t$F$_{2t}$—O(CF(CF$_3$)CF$_2$O)$_p$CF(CF$_3$)—, wherein t is 2, 3 or 4 and wherein m is 1 to 50, and p is 3 to 40.

80. A device according to item 79 as directly or indirectly dependent on item 60, or a component according to item 79 as directly or indirectly dependent on item 61, wherein R$_f$ is selected from the group consisting of —CF$_2$O(CF$_2$O)$_m$(C$_2$F$_4$O)$_p$CF$_2$—, —CF$_2$O(C$_2$F$_4$O)$_p$CF$_2$—, and —CF(CF$_3$)—(OCF$_2$CF(CF$_3$))$_p$O—(C$_1$F$_{2t}$)—O(CF(CF$_3$)CF$_2$O)$_p$CF(CF$_3$)—, and wherein t is 2, 3, or 4, and wherein the average value of m+p or p+p is from about 4 to about 24.

81. A device according to any one of items 72 to 80 as directly or indirectly dependent on item 60, or a component according to any one of items 72 to 80 as directly or indirectly dependent on item 61, wherein Q is selected from the group consisting of —C(O)N(R)—(CH$_2$)$_k$—, —S(O)$_2$N(R)—(CH$_2$)$_k$—, —(CH$_2$)$_k$—, —CH$_2$O—(CH$_2$)$_k$—, —C(O)S—(CH$_2$)$_k$—, —CH$_2$OC(O)N(R)—(CH$_2$)$_k$—, and

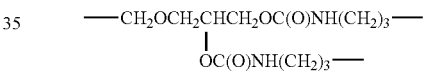

wherein R is hydrogen or C$_{1-4}$ alkyl, and k is 2 to about 25.

82. A device according to item 81 as directly or indirectly dependent on item 60, or a component according to item 81 as directly or indirectly dependent on item 61, wherein Q is selected from the group consisting of —C(O)N(R)(CH$_2$)$_2$—, —OC(O)N(R)(CH$_2$)$_2$—, —CH$_2$—O—(CH$_2$)$_2$—, or —CH$_2$—OC(O)N(R)—(CH$_2$)$_2$—, wherein R is hydrogen or C$_{1-4}$ alkyl and y is 1.

83. A device according to any one of items 72 to 82 as directly or indirectly dependent on item 60, or a component according to any one of items 72 to 82 as directly or indirectly dependent on item 61, wherein x is 0.

84. A device according to any one of items 64, 65, 72 to 83 as directly or indirectly dependent on item 60, or a component according to any one of items 64, 65, 72 to 83 as directly or indirectly dependent on item 61, wherein R is hydrogen.

85. A device according to any one of items 72 to 84 as directly or indirectly dependent on item 60, or a component according to any one of items 72 to 84 as directly or indirectly dependent on item 61, wherein R$_f$ is —CF$_2$O(CF$_2$O)$_m$(C$_2$F$_4$O)$_p$CF$_2$—, and Q-C(R)$_2$—Si(O—)$_{3-x}$(R$^{1a}$)$_x$ is C(O)NH(CH$_2$)$_3$Si(O—)$_3$.

86. A device according to item 60 or any one of items 62 to 85 as directly or indirectly dependent on item 60, or a component according to item 61 or any one of items 62 to 85 as directly or indirectly dependent on item 61, wherein the weight average molecular weight of the polyfluoropolyether segment is about 1000 or higher, in particular about 1800 or higher.

87. A device according to item 60 or any one of items 62 to 86 as directly or indirectly dependent on item 60, or a component according to item 61 or any one of items 62 to 86 as directly or indirectly dependent on item 61, wherein the amount of polyfluoropolyether silane entities having a polyfluoropolyether segment having a weight average molecular weight less than 750 is not more than 10% by weight of total amount of polyfluoropolyether silane entities, in particular not more than 5% by weight of total amount of polyfluoropolyether silane entities, more particularly not more than 1% by weight of total amount of polyfluoropolyether silane entities, and most particularly 0% by weight of total amount of polyfluoropolyether silane entities.

88. A device according to item 60 or any one of items 62 to 87 as directly or indirectly dependent on item 60, or a component according to item 61 or any one of items 62 to 87 as directly or indirectly dependent on item 61, wherein the polyfluoropolyether-containing coating has a thickness of at most about 300 nm, in particular at most about 200 nm, more particularly at most about 150 nm, and even more particularly at most about 100 nm.

89. A device according to item 60 or any one of items 62 to 88 as directly or indirectly dependent on item 60, or a component according to item 61 or any one of items 62 to 88 as directly or indirectly dependent on item 61, wherein the polyfluoropolyether-containing coating has a thickness of at least about 20 nm, in particular at least about 30 nm, and more particularly at least about 50 nm.

90. A device according to item 60 or any one of items 62 to 89 as directly or indirectly dependent on item 60, or a component according to item 61 or any one of items 62 to 89 as directly or indirectly dependent on item 61 according to item 37, wherein the polyfluoropolyether-containing coating comprises non-fluorinated cross-linking entities selected from the group consisting of entities of Formula IIb, entities of Formula IIIb or mixtures of entities of Formula IIb and Formula IIIb, wherein an entity of Formula IIb is an entity in accordance to the following Formula IIb:

$$Si(O-)_{4-g}(R^5)_g \qquad \text{IIb}$$

and an entity of Formula IIIb is an entity in accordance to the following Formula IIIb:

$$-L'-Q'C(R)_2Si(O-)_{3-g}-(R^5)_g \qquad \text{IIIb}$$

where L' represents a derivative of a reactive functional group;
Q' represents an organic divalent linking group;
each R is independently hydrogen or a $C_{1-4}$ alkyl group, and
where, for Formulas IIb and IIIb,
$R^5$ represents a non-hydrolysable group; and
g is 0, 1 or 2.

91. A device according to item 90 as directly or indirectly dependent on item 60, or a component according to item 90 as directly or indirectly dependent on item 61, wherein g is 0 or 1, in particular 0.

92. A device according to item 90 or item 91 as directly or indirectly dependent on item 60, or a component according to item 90 or item 91 as directly or indirectly dependent on item 61, wherein L' represents a derivative of a reactive functional group, said group selected from the group consisting of an amino group, an epoxy group, a mercaptan group, an anhydride group, vinyl ether group, vinyl ester group, allyl group, allyl ester group, vinyl ketone group, styrene group, vinyl amide group, acrylamide group, maleate group, fumarate group, acrylate group and methacrylate group.

93. A device or a component according to any one of items 60 to 92, as applicable, where said surface of the device or said surface of the component of the device, as applicable, is a surface that is or will come in contact with a medicament or a medicinal formulation during storage or delivery from the medicinal inhalation device.

94. A device or a component according to any one of items 60 to 93, as applicable, where said surface of the device or said surface of the component of the device, as applicable, is a surface that comes in contact with a movable component of the device or is a surface of a movable component of the device.

95. A device or a component according to any one of items 60 to 94, as applicable, wherein the device or the component, as applicable, is free of an undercoating.

96. A device or a component according to any one of items 60 to 95, as applicable, where said medicinal inhalation device is a metered dose inhaler or a dry powder inhaler.

97. A component according to item 59 or item 61 or any one of items 62 to 95 as directly or indirectly dependent on item 61, wherein the component is a component of a metered dose inhaler and the component is selected from the group consisting of an actuator, an aerosol container, a ferrule, a valve body, a valve stem and a compression spring.

98. A component according to item 59 or item 61 or any one of items 62 to 95 as directly or indirectly dependent on item 61, wherein the component is a component of a dry powder inhaler and the component is selected from the group consisting of a powder container, an component used to open sealed powder container, a component that defines at least in part a deagglomeration chamber, a component of a deagglomeration system, a component that defines at least in part a flow channel, a dose-transporting component, a component that defines at least in part a mixing chamber, a component that defines at least in part an actuation chamber, a mouthpiece and a nosepiece.

99. A component according to item 59 or item 61 or any one of items 62 to 95 as directly or indirectly dependent on item 61, wherein the component is a component of a breath-actuating device or a component of a breath-coordinating device or a spacer or a component of a spacer or a component of a dose counter for a medicinal inhalation device.

100. A device according to item 58 or item 60 or any one of items 62 to 96 as directly or indirectly dependent on item 60, wherein the device is a metered dose inhaler and the inhaler contains a medicinal aerosol formulation comprising a medicament and HFA 134a and/or HFA 227.

101. A device according to item 100, wherein the medicinal aerosol formulation is substantially free of ethanol.

102. A device according to item 101, wherein the medicinal aerosol formulation is free of ethanol.

103. A device according to any one of items 100 to 102, wherein the medicinal aerosol formulation is substantially free of surfactant.

104. A device according to item 103, wherein the medicinal aerosol formulation is free of surfactant.

105. A device according to any one of items 100 to 104, wherein the medicinal aerosol formulation comprises a medicament that is dispersed said formulation.

106. A device according to any one of items 100 to 105, wherein the medicinal aerosol formulation medicinal formulation comprises a medicament selected from the group consisting of albuterol, terbutaline, ipratropium, oxitropium, tiotropium, beclomethasone, flunisolide, budesonide, mometasone, ciclesonide, cromolyn sodium, nedocromil sodium, ketotifen, azelastine, ergotamine, cyclosporine, salmeterol, fluticasone, formoterol, procaterol, indacaterol, TA2005, omalizumab, zileuton, insulin, pentamidine, calcitonin, leuprolide, alpha-1-antitrypsin, interferon, triamcinolone, and pharmaceutically acceptable salts and esters thereof and mixtures thereof.

The above summary of the present invention is not intended to describe each disclosed embodiment or every implementation of the present invention. The description that follows more particularly exemplifies illustrative embodiments. In several places throughout the application, guidance is provided through lists of examples, which examples can be used individually and in various combinations. In each instance, the recited list serves only as a representative group and should not be interpreted as an exclusive list.

BRIEF DESCRIPTION OF DRAWINGS

The invention will now be described with reference to the accompanying drawings in which.

DETAILED DESCRIPTION

It is to be understood that the present invention covers all combinations of particular, suitable, desirable, favorable, advantageous and preferred aspects of the invention described herein.

Figure 1A:
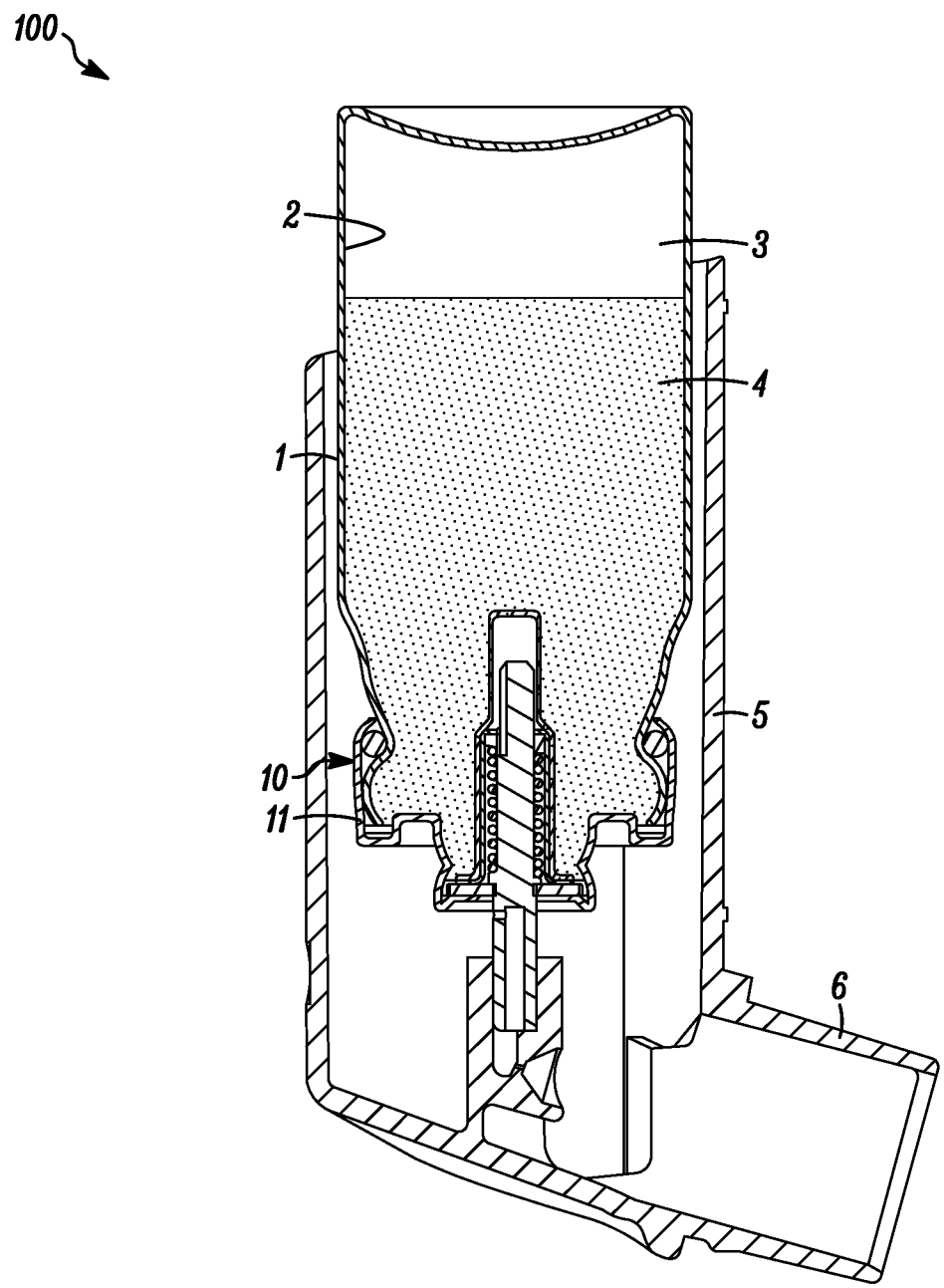
FIG. 1a represents a schematic cross-sectional view of a pressurized metered dose inhaler known in the art and FIG. 1b represents an enlarged view of a portion of the inhaler.

For better understanding of the present invention, in the following an exemplary, well known pressurized metered dose inhaler (FIG. 1) as well as several known metered dose valves for pressurized metered dose inhalers (FIGS. 2 to 5) will be first described. In particular, FIG. 1a shows a metered dose dispenser (100), in particular an inhaler, including an aerosol container (1) fitted with a metered dose valve (10) (shown in its resting position).

Aerosol containers for metered dose inhalers are typically made of aluminum or an aluminum alloy. Aerosol containers may be made of other materials, such as stainless steel, glass, plastic and ceramics.

Returning to FIG. 1a, the valve is typically affixed onto the container via a cap or ferrule (11) (typically made of aluminum or an aluminum alloy) which is generally provided as part of the valve assembly. The illustrated valve is a commercial valve marketed under the trade designation SPRAYMISER by 3M Company, St. Paul, Minn., USA. As shown in FIG. 1a, the container/valve dispenser is typically provided with an actuator (5) including an appropriate patient port (6), such as a mouthpiece. For administration to the nasal cavities the patient port is generally provided in an appropriate form (e.g. smaller diameter tube, often sloping upwardly) for delivery through the nose. Actuators are generally made of a plastic, for example polypropylene or polyethylene. As can be seen from FIG. 1a, the inner walls (2) of the container and the outer walls of the portion(s) of the metered dose valve located within the container defined a formulation chamber (3) in which aerosol formulation (4) is contained. Depending on the particular metered dose valve and/or filling system, aerosol formulation may be filled into the container either by cold-filling (in which chilled formulation is filled into the container and subsequently the metered dose valve is fitted onto the container) or by pressure filling (in which the metered dose valve is fitted onto the container and then formulation is pressure filled through the valve into the container).

An aerosol formulation typically comprises a medicament or a combination of medicaments and liquefied propellant selected from the group consisting of HFA 134a, HFA 227 and mixtures thereof. Aerosol formulations may, as desired or needed, comprise other excipients, such as surfactant, a co-solvent (e.g. ethanol), $CO_2$, or a particulate bulking agent. Medicament may be provided in particulate form (generally having a median size in the range of 1 to 10 microns) suspended in the liquefied propellant. Alternatively medicament may be in solution (e.g. dissolved) in the formulation. In the event a combination of two or more medicaments is included, all the medicaments may be suspended or in solution or alternatively one or more medicaments may be suspended, while one or more medicaments may be in solution. A medicament may be a drug, vaccine, DNA fragment, hormone or other treatment. The amount of medicament would be determined by the required dose per puff and available valve sizes, which are typically 25, 50 or 63 microlitres, but may include 100 microlitres where particularly large doses are required. Suitable drugs include those for the treatment of respiratory disorders, e.g., bronchodilators, anti-inflammatories (e.g. corticosteroids), anti-allergies, anti-asthmatics, anti-histamines, and anti-cholinergic agents. Therapeutic proteins and peptides may also be employed for delivery by inhalation. Exemplary drugs which may be employed for delivery by inhalation include but are not limited to: albuterol, terbutaline, ipratropium, oxitropium, tiotropium, beclomethasone, flunisolide, budesonide, mometasone, ciclesonide, cromolyn sodium, nedocromil sodium, ketotifen, azelastine, ergotamine, cyclosporine, salmeterol, fluticasone, formoterol, procaterol, indacaterol, TA2005, omalizumab, zileuton, insulin, pentamidine, calcitonin, leuprolide, alpha-1-antitrypsin, interferons, triamcinolone, and pharmaceutically acceptable salts and esters thereof such as albuterol sulfate, formoterol fumarate, salmeterol xinafoate, beclomethasone dipropionate, triamcinolone acetonide, fluticasone propionate, tiotropium bromide, leuprolide acetate and mometasone furoate.

Embodiments, described in detail below, in accordance with the present invention are particularly useful in regard to metered dose inhalers including an medicinal aerosol formulation that include low amounts of surfactant (0.005 wt % with respect to the formulation); or is substantially free (less than 0.0001 wt % with respect to drug) or free of a surfactant. Alternatively or additionally, embodiments described in detail below, are particularly useful in metered dose inhalers including a medicinal aerosol formulation that contains low amounts of ethanol (less than 5 wt % with respect to the formulation), or is substantially free (less than 0.1 wt % with respect to the formulation) or free of ethanol.

Figure 1B:
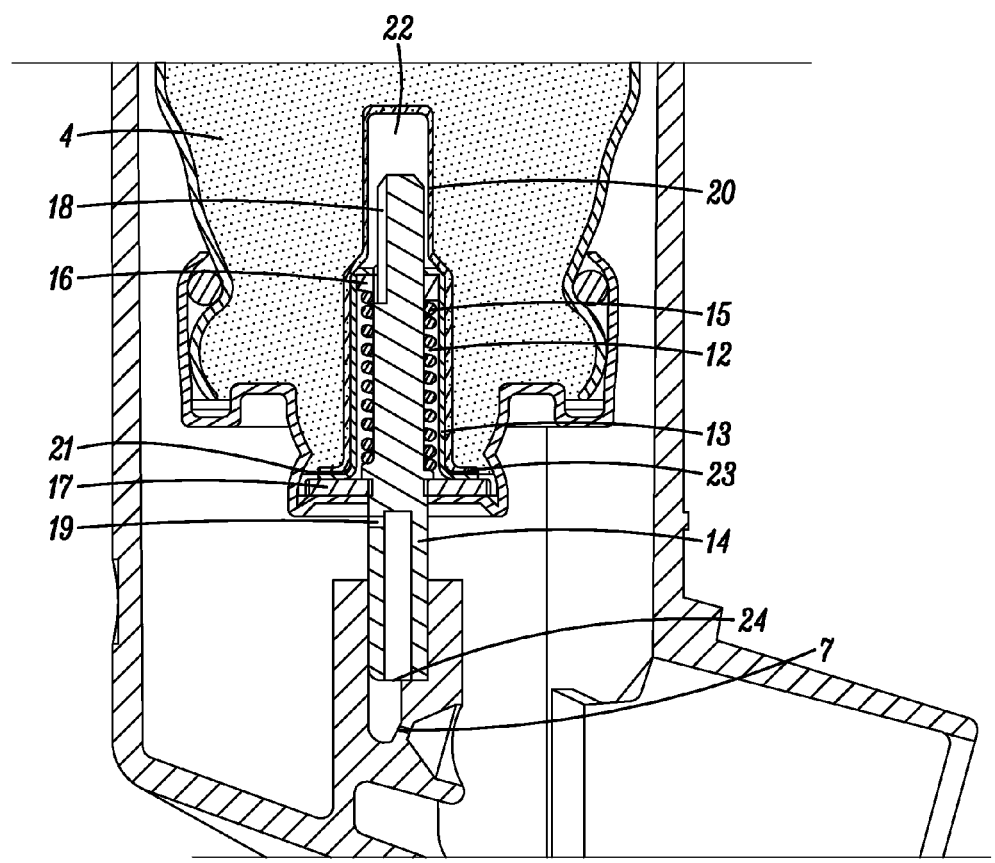
Figure 2:
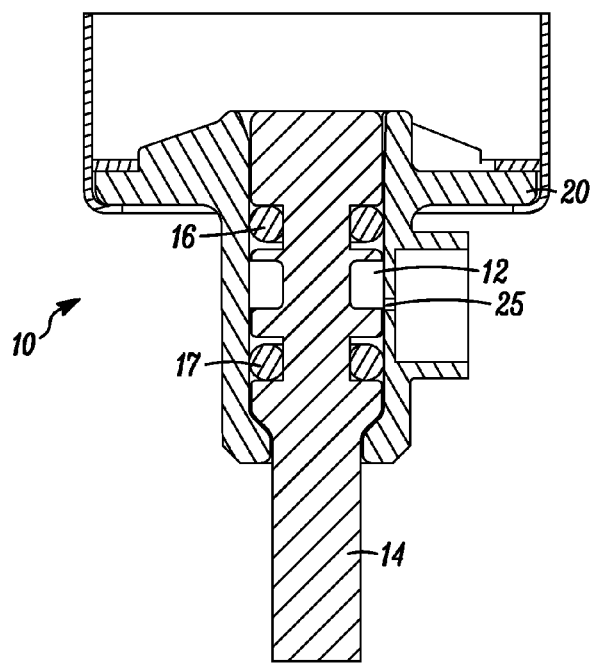
FIGS. 2 to 5 represent schematic cross-sectional views of further metered dose valves known in the art for use in pressurized metered dose inhalers.
Figure 3:
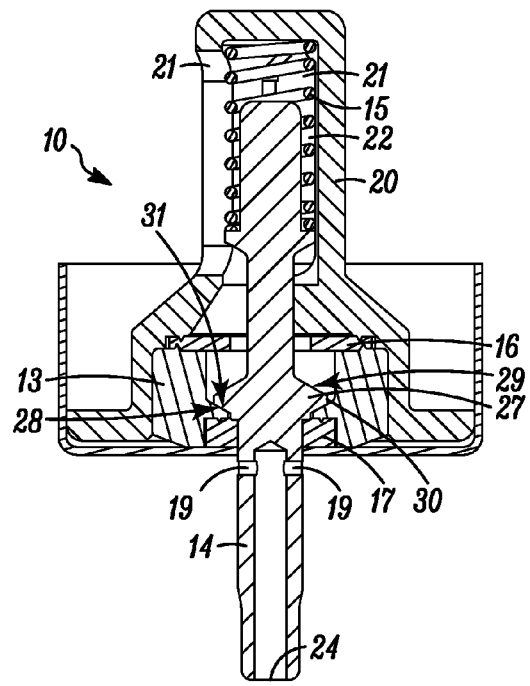
Figure 4:
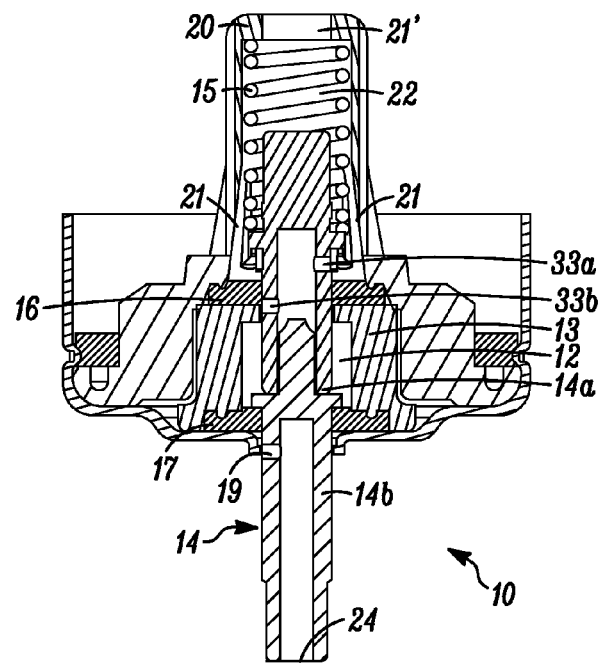
Figure 5:
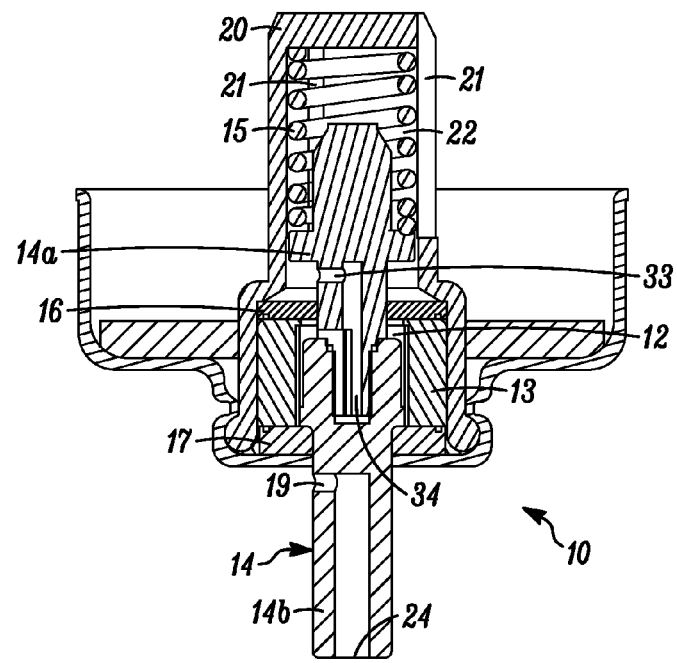

The valve shown in FIG. 1a, better viewed in FIG. 1b, includes a metering chamber (12), defined in part by an inner valve body (13), through which a valve stem (14) passes. The valve stem, which is biased outwardly by a compression spring (15), is in sliding sealing engagement with an inner tank seal (16) and an outer diaphragm seal (17). The valve also includes a second valve body (20) in the form of a bottle emptier.

(For the sake of clarity in the description of various metered dose valves, in particular those including at least two valve bodies, in the following a valve body defining in part the metering chamber will be referred to as a "primary" valve body, while other types of valve body, e.g. defining a pre-metering region, a pre-metering chamber, a spring cage and/or a bottle emptier will be referred to as a "secondary" valve body.)

Returning to FIG. 1a, aerosol formulation (4) can pass from the formulation chamber into a pre-metering chamber (22) provided between the secondary valve body (20) and the primary valve body (13) through an annular space (21) between the flange (23) of the secondary valve body and the primary valve body. To actuate (fire) the valve, the valve stem (14) is pushed inwardly relative to the container from its resting position shown in FIGS. 1a and b, allowing formulation to pass from the metering chamber through a side hole (19) in the valve stem and through a stem outlet (24) to an actuator nozzle (7) then out to the patient. When the valve stem (14) is released, formulation enters into the valve, in particular into the pre-metering chamber (22), through the annular space (21) and thence from the pre-metering chamber through a groove (18) in the valve stem past the tank seal (16) into the metering chamber (12).

As mentioned above, FIGS. 2 to 5 show other known metered dose valves used in pMDIs. Similar to the valve shown in FIG. 1, the valves of FIGS. 2 to 5 are typically fitted via a ferrule onto an aerosol container whereby a formulation chamber is defined by the inner walls of the container and the outer walls of the portion(s) of the valve located within the container. For the sake of ease in understanding and comparison, similar components of the respective valves are identified with like reference numbers in the Figures.

FIG. 2 shows a metered dose valve (10) of a type generally similar to that disclosed and described in U.S. Pat. No. 5,772,085 (incorporated herein by reference). The valve is shown in its resting position and includes a valve body (20) and a valve stem (14). The valve stem, which is biased outwardly under the pressure of the aerosol formulation contained within the formulation container, is provided with an inner seal and an outer seal (16 and 17). Unlike the valves in FIG. 1 and FIGS. 3 to 5, which are push-to-fire type valves, the valve here is a release-to-fire type valve. To actuate the valve, the valve stem (14) is first pushed upwards into the formulation chamber (not shown), so that the outer seal (17) passes inwardly beyond an outlet (25) provided in the external portion of the valve body and the inner seal (16) then passes inwardly and disengages from the inner walls of the valve body, thus bringing the metering chamber (12) up into the formulation chamber so that formulation can enter the metering chamber (referred to as the priming position of the valve) and then the valve stem is released moving outwardly so that the inner seal re-engages the valve body and the outer seal then passes outwardly beyond the outlet, bringing the metering chamber in communication with the outlet, so that formulation passes through the outlet to the patient.

FIG. 3 shows a metered dose valve (10) of the type generally similar to that disclosed and described in WO 2004/022142 (incorporated herein by reference). The valve is shown in its resting position and includes a secondary valve body (20) and a valve stem (14) that is biased outwardly by a compression spring (15). The valve is provided with an inner seal (16) and outer diaphragm seal (17), with the valve stem being in sliding sealing engagement with the diaphragm seal. In this valve, the secondary valve body is in the form of a spring cage housing having three slots (21, two visible) providing communication between the formulation chamber (not shown) and a pre-metering chamber (22). This valve includes a transitory metering chamber formed upon actuation of the valve. During actuation of the valve, as the valve stem (14) is pushed inwardly relative to the container, a metering chamber (12, not visible) is formed between a lower surface (28) of a conical portion (27) of the valve stem (14) and an upper, sloping surface (31) of a primary valve body (13). Aerosol formulation passes around the shoulder (30) of the conical portion of the valve stem into the forming metering chamber and as the valve stem is further pushed in the upper surface (29) of the conical portion forms a face seal with the inner seal (16), thereby sealing off the metering chamber. As the valve stem is yet further displaced inwardly, formulation is allowed to pass from the metering chamber through side holes (19) in the valve stem and through a stem outlet (24) in the valve stem, and subsequently out to the patient typically via an actuator nozzle (7, not shown).

FIG. 4 shows a commercial metered dose valve supplied by Bespak, Bergen Way, King's Lynn, Norfolk, PE30 2JJ, UK under the trade designation BK357, in its resting position. The valve includes a secondary valve body (20) in the form of a spring cage with two slots (21) and an opening at the top (21') allowing communication between the formulation chamber (not shown) and a pre-metering chamber (22). The valve also includes a valve stem (14), made of two components (14*a*, 14*b*), which is biased outwardly by a compression spring (15) and passes through a metering chamber (12) defined in part by a primary valve body (13). The valve stem is in sliding sealing engagement with an inner seal (16) and an outer diaphragm seal (17). Aerosol formulation can pass from the pre-metering chamber (22) into the metering chamber (12) via side holes (33*a*, 33*b*) in the upper portion (14*a*) of the stem (14). Similar to the valve shown in FIG. 1, to actuate (fire) the valve, the valve stem (14) is pushed inwardly relative to the container, allowing a metered dose of formulation to pass from the metering chamber through a side hole (19) in the valve stem and through a stem outlet (24) and then typically through an actuator nozzle (7, not shown) out to the patient.

FIG. 5 shows a commercial metered dose valve supplied by Valois SAS, Pharmaceutical Division, Route des Falaises, 27100 le Vaudreuil, France under the trade designation RCS, in its resting position. The valve includes a secondary valve body (20) in the form of a spring cage with three slots (21, two visible) allowing communication between the formulation chamber (not shown) and a pre-metering chamber (22). The valve also include a valve stem (14), made of two components (14*a*, 14*b*), which is biased outwardly by a compression spring (15) and passes through a metering chamber (12) defined in part by a primary valve body (13). The valve stem is in sliding sealing engagement with an inner seal (16) and an outer diaphragm seal (17). Aerosol formulation can pass from the pre-metering chamber (22) into the metering chamber through a side hole (33) and an internal channel (34) provided in the upper portion (14*a*) of the valve stem. Similar to the valve shown in FIG. 1, to actuate (fire) the valve, the valve stem (14) is pushed inwardly relative to the container, allowing formulation to pass from the metering chamber through a side hole (19) in the valve stem and through a stem outlet (24) and then typically through an actuator nozzle (7, not shown) out to the patient.

With the exception of the elastomeric seals used in metered dose valves, typically the components of such valves are made of metal (e.g. stainless steel, aluminum or aluminum alloy) or plastic. For example compression springs are generally made of a metal, in particular stainless steel as the conventional material. Compression springs may also be made of aluminum or aluminum alloy. Valve stems and valve bodies are generally made of metal and/or plastic; as a metal conventionally stainless steel is used (other metals that may be used include aluminum, aluminum alloy and titanium) and as plastics conventionally polybutylene terephthalate (PBT) and/or acetal are used (other polymers that may be used include polyetheretherketones, nylon, other polyesters (such as tetrabutylene terephthalate), polycarbonates and polyethylene).

Favorably at least a portion of a surface, more favorably the entire surface, of a component or components of a medicinal inhalation device (e.g. aerosol containers, actuators, ferrules, valve bodies, valve stems or compression springs of metered dose inhalers or powder containers of dry powder inhalers) which is or will come in contact with a medicament or a medicinal formulation during storage or delivery from the medicinal inhalation device are treated according to methods described herein. Most favorably the entire surface of the component, including any surface or surfaces (if present) that do not or will not come in contact with a medicament or a medicinal formulation during storage or delivery from the device, are treated according to methods described herein. Alternatively or additionally, favorably at least a portion of a surface, more favorably the entire surface, of a component or components of a medicinal inhalation device, which either come in contact with a movable component or are movable during storage or delivery from the medicinal inhalation device are treated according to methods described herein. Examples of such components for metered dose inhalers include e.g. valve bodies, valve stems or compression springs of metered dose valves.

In particular a component of a medicinal inhalation device in accordance with the present invention or made according to methods in accordance with the present invention is a component of a metered dose inhaler. Said component may be selected from the group consisting of aerosol container, an actuator, a ferrule, a valve body (e.g. a primary and/or a secondary valve body), a valve stem and a compression spring. Alternatively a component of a medicinal inhalation device in accordance with the present invention or made according to methods in accordance with the present invention is a component of a dry powder inhaler. Said component may be selected from the group consisting of a component that defines at least in part a powder container (e.g. a multi-dose reservoir container or single dose blister or capsule), an component used to open a sealed powder container (e.g. piercer to open single dose blisters or capsules), a component that defines at least in part a deagglomeration chamber, a component of a deaglomeration system, a component that defines at least in part a flow channel, a dose-transporting component (e.g. a dosing rod, dosing wheel or dosing cylinder with a recess dimensioned to accommodate a single dose of powder trapped between said component and a housing in which it moves to transport the dose), a component that defines at least in part a mixing chamber, a component that defines at least in part an actuation chamber (e.g. a holding chamber where a dose is dispensed prior to inhalation), a mouthpiece and a nosepiece.

Embodiments in accordance with certain aspects of the present invention include applying onto at least a portion of a surface of a medicinal inhalation device or a component of a medicinal inhalation device (e.g. an aerosol container of a metered dose inhaler, a metered dose valve or a component thereof, or a powder container of a dry powder inhaler), a composition comprising a multifunctional polyfluoropolyether silane, in particular a difunctional polyfluoropolyether silane.

As mentioned above, the term "multifunctional polyfluoropolyether silane" as used herein is generally understood to mean a multivalent polyfluoropolyether segment functionalized with a multiple of functional silane groups, and the term "difunctional polyfluoropolyether silane" as used herein is generally understood to mean a divalent polyfluoropolyether segment functionalized with a multiple of functional silane groups (in particular two to four functional silane groups, more particular two functional silane groups.

In compositions for application to said surface, the silane groups of the multifunctional polyfluoropolyether silane favorably include at least one hydrolysable group (e.g. hydrolysable in the presence of water, optionally under acidic or basic conditions producing groups capable of undergoing a condensation reaction, for example silanol groups), more favorably at least two hydrolysable groups, and most favorably three hydrolysable groups. The hydrolyzable groups may be the same or different. Desirably a hydrolysable group is a group selected from the group consisting of hydrogen, halogen, alkoxy, acyloxy, aryloxy, and polyalkyleneoxy, more desirably a group selected from the group consisting of alkoxy, acyloxy, aryloxy, and polyalkyleneoxy, even more desirably a group selected from the group consisting of alkoxy, acyloxy and aryloxy, and most desirably an alkoxy group (e.g. OR' wherein each R' is independently a $C_{1-6}$ alkyl, in particular a $C_{1-4}$ alkyl).

Application of a composition comprising a multifunctional polyfluoropolyether silane as described herein allows for effective and efficient provision of a highly desirable polyfluoropolyether-containing coating onto said surface of the medicinal inhalation device or said surface of a component of such a device. In particular such a coating comprising multifunctional polyetherpolyether silane shows extensive bonding (e.g. covalent bonding) to said surface and cross-linking within the polyfluoropolyether-containing coating itself, providing very desirable structural integrity over the lifetime of the medicinal inhalation device.

As mentioned above, the application of compositions comprising multifunctional polyfluoropolyether silanes as described herein is also advantageous in that said application allows the provision of very thin polyfluoropolyether-containing coatings, which although very thin have desirable surface properties together with advantageous structural integrity over the lifetime of the medicinal inhalation device. Preferably the thickness of the polyfluoropolyether-containing coating is at most about 300 nm, more preferably at most about 200 nm, even more preferably at most about 150 nm, and most preferably at most about 100 nm. For certain of these embodiments, the thickness of the polyfluoropolyether-containing coating is at least about 20 nm, preferably at least about 30 nm, and most preferably at least about 50 nm.

Embodiments in accordance with other aspects of the present invention include a medicinal inhalation device or a component of a medicinal inhalation device, said device or component comprising a polyfluoropolyether-containing coating bonded to at least a portion of a surface of the device or component, respectively, said polyfluoropolyether-containing coating comprising a plurality of cross-linked, multifunctional polyfluoropolyether-silane entities and said polyfluorpolyether-containing coating sharing at least one covalent bond with said surface.

Favorably the at least one shared covalent bond includes a bond in a —O—Si group.

Favorably the polyfluoropolyether-containing coating shares a plurality of covalent bonds with the surface of the device or component, respectively.

As mentioned above, for enhanced stability and/or resistance to attack (e.g. by ethanol, drug, and/or other potential components of medicinal inhalation formulations) desirably the polyfluoropolyether segment is not linked to silane groups via a functionality that includes a nitrogen-silicon bond or a sulfur-silicon bond. In particular, for enhanced stability and resistance of the applied polyfluoropolyether-containing coating to attack, it is desirable that polyfluoropolyether segment is linked to silane groups via a functionality that include a carbon-silicon bond, more particularly via a —C(R)$_2$—Si functionality where R is independently hydrogen or a C$_{1-4}$ alkyl group, and most particular, via a —(C(R)$_2$)$_k$—C(R)$_2$—Si functionality where k is at least 2 (preferably 2 to about 25, more preferably 2 to about 15, most preferably 2 to about 10). The inclusion of —(C(R)$_2$)$_k$— where k is at least 2 advantageously, additionally provides flexural strength. Preferably R is hydrogen.

As mentioned above, for enhanced surface properties as well as coating efficiency, preferably the polyfluoropolyether segment is a perfluorinated polyfluoropolyether segment. The use of polyfluoropolyether segments including perfluorinated repeating units including short chains of carbon, where desirably the number of carbon atoms in sequence is at most 6, more desirably at most 4, even more desirably at most 3, and most desirably at most 2, additionally facilitating durability/flexibility of the applied polyfluoropolyether-containing coating as well as minimizing a potential of bioaccumulation of perfluorinated moieties.

As mentioned above, for certain embodiments, the weight average molecular weight of the polyfluoropolyether segment is about 1000 or higher, more desirably about 1800 or higher. Higher weight average molecular weights further facilitate durability as well as minimizing a potential of bioaccumulation. Generally for ease in use and application, the weight average molecular weight of the polyfluoropolyether segment is desirably about 6000 at most and more desirably about 4000 at most.

Polyfluoropolyether silanes typically include a distribution of oligomers and/or polymers. Desirably for facilitation of structural integrity of polyfluoropolyether-containing coating as well as minimization of a potential of bioaccumulation, the amount of polyfluoropolyether silane (in such a distribution) having a polyfluoropolyether segment having a weight average molecular weight less than 750 is not more than 10% by weight (more desirably not more than 5% by weight, and even more desirably not more 1% by weight and most desirable 0%) of total amount of polyfluoropolyether silane in said distribution.

For certain favorable embodiments, the composition comprising a multifunctional polyfluoropolyether silane is a composition comprising a multifunctional polyfluoropolyether silane of the Formula Ia:

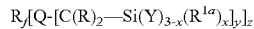
                                    Ia wherein:
R$_f$ is a multivalent polyfluoropolyether segment;
Q is an organic divalent or trivalent linking group;
each R is independently hydrogen or a C$_{1-4}$ alkyl group;
each Y is independently a hydrolysable group;
R$^{1a}$ is a C$_{1-8}$ alkyl or phenyl group;
x is 0 or 1 or 2;
y is 1 or 2; and
z is 2, 3, or 4.

Application of compositions comprising polyfluoropolyether silanes in accordance with Formula Ia favorably allows the provision of medicinal inhalation devices or components thereof comprising a polyfluoropolyether-containing coating bonded (e.g. covalently bonded) onto at least a portion of surface of the device or component, as applicable, wherein the polyfluoropolyether-containing coating comprises multifunctional polyfluoropolyether silane entities of the following Formula Ib:

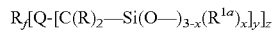
                                    Ib wherein:
R$_f$ is multivalent polyfluoropolyether segment;
Q is an organic divalent or trivalent linking group;
each R is independently hydrogen or a C$_{1-4}$ alkyl group;
R$^{1a}$ is a C$_{1-8}$ alkyl or phenyl group;
X is 0 or 1 or 2;
y is 1 or 2; and
z is 2, 3, or 4.

Desirably the at least one covalent bond shared with the surface of the medicinal inhalation device or the surface of a component of a medicinal inhalation device, as applicable, includes a bond to an oxygen atom in Si(O—)$_{3-x}$.

Advantageously such polyfluoropolyether-containing coatings are typically transparent or translucent.

The multivalent polyfluoropolyether segment, R$_f$, includes linear, branched, and/or cyclic structures, that may be saturated or unsaturated, and includes two or more in-chain oxygen atoms. R$_f$ is preferably a perfluorinated group (i.e., all C—H bonds are replaced by C—F bonds). However, hydrogen atoms may be present instead of fluorine atoms provided that not more than one atom of hydrogen is present for every two carbon atoms. When hydrogen atoms are present, preferably, R$_f$ includes at least one perfluoromethyl group.

For certain embodiments, the multivalent polyfluoropolyether segment, R$_f$, comprises perfluorinated repeating units selected from the group consisting of —(C$_n$F$_{2n}$)—, —(C$_n$F$_{2n}$O)—, —(CF(Z))—, —(CF(Z)O)—, —(CF(Z)C$_n$F$_{2n}$O)—, —(C$_n$F$_{2n}$CF(Z)O)—, —(CF$_2$CF(Z)O)—, and combinations thereof; wherein n is an integer from 1 to 6; Z is a perfluoroalkyl group, an oxygen-containing perfluoroalkyl group, a perfluoroalkoxy group, or an oxygen-substituted perfluoroalkoxy group, each of which can be linear, branched, or cyclic, and have 1 to 5 carbon atoms and up to 4 oxygen atoms when oxygen-containing or oxygen-substituted. For units comprising Z it is desirable that the total number of carbon atoms in sequence per unit is at most 6 (more desirably at most 4, and most desirably at most 3). Being oligomeric or polymeric in nature, these compounds exist as mixtures and are suitable for use as such. The perfluorinated repeating units may be arranged randomly, in blocks, or in an alternating sequence. Favorably, the polyfluoropolyether segment comprises perfluorinated repeating units selected from the group consisting of —(C$_n$F$_{2n}$O)—, —(CF(Z)O)—, —(CF(Z)C$_n$F$_{2n}$O)—, —(C$_n$F$_{2n}$CF(Z)O)—, —(CF$_2$CF(Z)O)—, and combinations thereof; and more favorably perfluorinated repeating units selected from the group consisting of —(C$_n$F$_{2n}$O)—, —(CF(Z)O)—, and combinations thereof. For certain of these embodiments, n is an integer from 1 to 4; or 1 to 3; or 1 or 2. For certain of these embodiments, Z is a —CF$_3$ group.

R$_f$ is preferably divalent, and z is 2. For certain of these embodiments, the approximate average structure of R$_f$ is selected from the group consisting of —CF$_2$O(CF$_2$O)$_m$(C$_2$F$_4$O)$_p$CF$_2$—, —CF$_2$O(C$_2$F$_4$O)$_p$CF$_2$—, —CF(CF$_3$)O(CF(CF$_3$)CF$_2$O)$_p$CF(CF$_3$)—, —(CF$_2$)$_3$O(C$_4$F$_8$O)$_p$(CF$_2$)$_3$—, —CF(CF$_3$)—(OCF$_2$CF(CF$_3$))$_p$O—C$_t$F$_{2t}$—O(CF(CF$_3$)CF$_2$O)$_p$CF(CF$_3$)— (wherein t is 2 to 4), and wherein m is 1 to 50, and p is 3 to 40. For certain of these embodiments, R$_f$ is selected from the group consisting of —CF$_2$O(CF$_2$O)$_m$(C$_2$F$_4$O)$_p$CF$_2$—, —CF$_2$O(C$_2$F$_4$O)$_p$CF$_2$—, and —CF(CF$_3$)—(OCF$_2$CF(CF$_3$))$_p$O—(C$_t$F$_{2t}$)—O(CF(CF$_3$)CF$_2$O)$_p$CF(CF$_3$)—, and wherein t is 2, 3 or 4, and the average value of m+p or p+p or p is from about 4 to about 24.

The above structures are approximate average structures where p and m designate the number of randomly distributed perfluorinated repeating units. Further, as mentioned above polyfluoropolyether silanes described herein typically include a distribution of oligomers and/or polymers, so p and/or m may be non-integral and where the number is the approximate average is over this distribution.

The organic divalent or trivalent linking group, Q, can include linear, branched, or cyclic structures that may be saturated or unsaturated. The organic divalent or trivalent linking group, Q, optionally contains one or more heteroatoms selected from the group consisting of sulfur, oxygen, and nitrogen, and/or optionally contains one or more functional groups selected from the group consisting of esters, amides, sulfonamides, carbonyl, carbonates, ureylenes, and carbamates. Again for flexural strength Q favorably includes a segment with not less than 2 carbon atoms, said segment of Q being directly bonded to the —C(R)$_2$-group of the silane-containing moiety (i.e. for Formula Ia —C(R)$_2$—Si(Y)$_{3-x}$(R$^{1a}$)$_x$ and for Formula Ib —C(R)$_2$—Si(O—)$_{3-x}$(R$^{1a}$)$_x$). For such embodiments generally Q includes not more than about 25 carbon atoms. Q is preferably substantially stable against hydrolysis and other chemical transformations, such as nucleophilic attack. When more than one Q groups are present, the Q groups can be the same or different.

For certain embodiments, including any one of the above embodiments, Q includes organic linking groups such as —C(O)N(R)—(CH$_2$)$_k$—, —S(O)$_2$N(R)—(CH$_2$)$_k$—, —(CH$_2$)$_k$—, —CH$_2$O—(CH$_2$)$_k$—, —C(O)S—(CH$_2$)$_k$—, —CH$_2$OC(O)N(R)—(CH$_2$)$_k$—, and

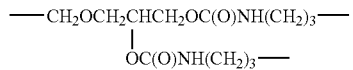

wherein R is hydrogen or C$_{1-4}$ alkyl, and k is 2 to about 25. For certain of these embodiments, k is 2 to about 15 or 2 to about 10.

Favorably Q is a divalent linking group, and y is 1. In particular, Q is favorably a saturated or unsaturated hydrocarbon group including 1 to about 15 carbon atoms and optionally containing 1 to 4 heteroatoms and/or 1 to 4 functional groups. For certain of these embodiments, Q is a linear hydrocarbon containing 1 to about 10 carbon atoms, optionally containing 1 to 4 heteroatoms and/or 1 to 4 functional groups. For certain of these embodiments, Q contains one functional group. For certain of these embodiments, Q is preferably —C(O)N(R)(CH$_2$)$_2$—, —OC(O)N(R)(CH$_2$)$_2$—, —CH$_2$—O—(CH$_2$)$_2$—, or —CH$_2$—OC(O)N(R)—(CH$_2$)$_2$—, wherein R is hydrogen or C$_{1-4}$ alkyl.

For certain favorable embodiments, including any embodiment described herein where R is present, R is hydrogen.

Favorably x in the silane-containing moiety (i.e. for Formula Ia —C(R)$_2$—Si(Y)$_{3-x}$(R$^{1a}$)$_x$ and for Formula Ib —C(R)$_2$—Si(O—)$_{3-x}$(R$^{1a}$)$_x$) is 0.

The hydrolyzable groups, Y, of Formula Ia may be the same or different and are capable of hydrolyzing, for example, in the presence of water, optionally under acidic or basic conditions, producing groups capable of undergoing a condensation reaction, for example silanol groups. Desirably, each Y of Formula Ia is independently a group selected from the group consisting of hydrogen, halogen, alkoxy, acyloxy, aryloxy, and polyalkyleneoxy, more desirably each Y is independently a group selected from the group consisting of alkoxy, acyloxy, aryloxy, and polyalkyleneoxy, even more desirably each Y is independently a group selected from the group consisting of alkoxy, acyloxy and aryloxy, and most desirably each Y is independently an alkoxy group.

For certain embodiments, including any relevant embodiment described herein:
Favorably alkoxy is —OR', and acyloxy is —OC(O)R', wherein each R' is independently a lower alkyl group, optionally substituted by one or more halogen atoms. For certain embodiments, R' is preferably C$_{1-6}$ alkyl and more preferably C$_{1-4}$ alkyl. R' can be a linear or branched alkyl group.
Favorably aryloxy is —OR" wherein R" is aryl optionally substituted by one or more substituents independently selected from halogen atoms and C$_{1-4}$ alkyl optionally substituted by one or more halogen atoms. For certain embodiments, R" is preferably unsubstituted or substituted C$_{6-12}$ aryl and more preferably unsubstituted or substituted C$_{6-10}$ aryl.
Favorably polyalkyleneoxy is —O—(CHR$^4$—CH$_2$O)$_q$—R$^3$ wherein R$^3$ is C$_{1-4}$ alkyl, R$^4$ is hydrogen or methyl, with at least 70% of R$^4$ being hydrogen, and q is 1 to 40, preferably 2 to 10.

For certain particularly favored embodiments, including any one of the above embodiments including a compound in accordance with Formula Ia, R$_f$ is —CF$_2$O(CF$_2$O)$_m$(C$_2$F$_4$O)$_p$CF$_2$— and Q-C(R)$_2$—Si(Y)$_{3-x}$(R$^{1a}$)$_x$ is C(O)NH(CH$_2$)$_3$Si(OR')$_3$ wherein R' is methyl or ethyl. For certain particular favored embodiments, including any one of the above embodiments including an entity in accordance with Formula Ib, R$_f$ is —CF$_2$O(CF$_2$O)$_m$(C$_2$F$_4$O)$_p$CF$_2$— and Q-C(R)$_2$—Si(O—)$_{3-x}$(R$^{1a}$)$_x$ is C(O)NH(CH$_2$)$_3$Si(O—)$_3$. For certain of these embodiments, m and p are each about 9 to 12.

Compounds in accordance with Formula Ia as described above can be synthesized using standard techniques. For example, commercially available or readily synthesized perfluoropolyether esters (or functional derivatives thereof) can be combined with a functionalized alkoxysilane, such as a 3-aminopropylalkoxysilane, according to U.S. Pat. No. 3,810,874 (Mitsch et al.).

For certain embodiments, the multifunctional polyfluoropolyether silane is desirably applied as a composition comprising the multifunctional polyfluoropolyether silane and an organic solvent. The organic solvent or blend of organic solvents used typically is capable of dissolving at least about 0.01 percent by weight of the multifunctional polyfluoropolyether silane, in particular one or more silanes of the Formula Ia. It is desirable that the solvent or mixture of solvents have a solubility for water of at least about 0.1 percent by weight, and for certain of these embodiments, a solubility for acid of at least about 0.01 percent by weight.

Suitable organic solvents, or mixtures of solvents can be selected from aliphatic alcohols, such as methanol, ethanol, and isopropanol; ketones such as acetone and methyl ethyl ketone; esters such as ethyl acetate and methyl formate; ethers such as diethyl ether, diisopropyl ether, methyl t-butyl ether and dipropyleneglycol monomethylether (DPM); hydrocarbon solvents such as alkanes, for example, heptane, decane, and paraffinic solvents; fluorinated hydrocarbons such as perfluorohexane and perfluorooctane; partially fluorinated hydrocarbons, such as pentafluorobutane; hydrofluoroethers such as methyl perfluorobutyl ether and ethyl perfluorobutyl ether. For certain embodiments, including any one of the above embodiments, the organic solvent is a fluorinated solvent, which includes fluorinated hydrocarbons, partially fluorinated hydrocarbons, and hydrofluoroethers. For certain of these embodiments, the fluorinated solvent is a hydrofluoroether. For certain of these embodiments, the hydrofluoroether is methyl perfluorobutyl ether. For certain embodiments, including any one of the above embodiments except where the organic solvent is a fluorinated solvent, the organic solvent is a lower alcohol. For certain of these embodiments, the lower alcohol is selected from the group consisting of methanol, ethanol, isopropanol, and mixtures thereof. For certain of these embodiments, the lower alcohol is ethanol.

For certain embodiments, including any one of the above embodiments where the organic solvent is a lower alcohol, the composition favorably further comprises an acid. For certain of these embodiments, the acid is selected from the group consisting of acetic acid, citric acid, formic acid, triflic acid, perfluorobutyric acid, sulfuric acid, and hydrochloric acid. For certain of these embodiments, the acid is hydrochloric acid.

For certain embodiments, e.g. compositions including a hydrolysable group, the composition may further comprise water.

Compositions comprising multifunctional polyfluoropolyether silane as described herein, may advantageously further comprise a non-fluorinated cross-linking agent that is capable of engaging in a cross-linking reaction. Preferably such a cross-linking agent comprises one or more non-fluorinated compounds, each compound being independently selected from the group consisting of:
a non-fluorinated compound having at least two hydrolysable groups (more preferably at least three hydrolysable groups, and most preferably four hydrolysable groups), and a non-fluorinated compound having at least one reactive functional group and at least one hydrolysable group (more preferably at least one reactive functional group and at least two hydrolysable groups, and most preferably at least one reactive functional group and three hydrolysable groups). Hydrolysable groups, if two or more are present may be the same or different. Hydrolysable groups are generally capable of hydrolyzing under appropriate conditions, for example under acidic or basic aqueous conditions, such that the linking agent can undergo condensation reactions. Preferably, the hydrolysable groups upon hydrolysis yield groups capable of undergoing condensation reactions. Typical and preferred examples of hydrolysable groups include those as described above, e.g. with respect to Formula Ia. Preferably, hydrolysable groups are independently an alkoxy, —$OR^6$, more preferably an alkoxy where $R^6$ is a $C_{1-4}$ alkyl. A reactive functional group may react by condensation or addition reactions (e.g. an amino group, an epoxy group, a mercaptan group or an anhydride group) or by free-radical polymerization (e.g. a vinyl ether group, a vinyl ester group, an allyl group, an allyl ester group, a vinyl ketone group, a styrene group, a vinyl amide group, an acrylamide group, a maleate group, a fumarate group, an acrylate group or a methacrylate group).

Advantageously such a cross-linking agent comprises one or more non-fluorinated compounds of silicon having either at least two hydrolysable groups or at least one reactive functional group and at least one hydrolysable per molecule. Preferably such a non-fluorinated compound of silicon is a compound in accordance to Formula IIa or Formula IIIa:

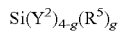   IIa where $R^5$ represents a non-hydrolysable group;
$Y^2$ represents a hydrolysable group; and
g is 0, 1 or 2;

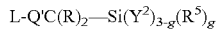   IIIa where L represents a reactive functional group;
Q' represents an organic divalent linking group;
R is independently hydrogen or a $C_{1-4}$ alkyl group;
$R^5$ represents a non-hydrolysable group;
$Y^2$ represents a hydrolysable group; and
g is 0, 1 or 2.

Cross-linking agents may favorably comprise a mixture of a non-fluorinated silicon compound in accordance with Formula IIa and a non-fluorinated silicon compound in accordance with Formula IIIa.

The non-hydrolysable group $R^5$ is generally not capable of hydrolyzing under the conditions used during application of the composition comprising the multifunctional polyfluoropolyether silane. For example, the non-hydrolysable group $R^5$ may be independently selected from a hydrocarbon group. If g is 2, the non-hydrolysable groups may the same or different. Preferably g is 0 or 1, more preferably g is 0. $Y^2$ represents a hydrolysable group as described above, and as described hydrolysable groups may be the same or different. Preferably, the hydrolysable groups upon hydrolysis yield silanol groups capable of undergoing condensation reactions. Preferably, hydrolysable groups are independently an alkoxy, —$OR^6$, more preferably an alkoxy where $R^6$ is a $C_{1-4}$ alkyl.

Representative examples of favorable non-fluorinated silicon compounds in accordance with Formula IIa for use in a cross-linking agent include tetramethoxysilane, tetraethoxysilane, tetrapropoxysilane, tetrabutoxysilane, methyl triethoxysilane, dimethyldiethoxysilane, octadecyltriethoxysilane, and mixtures thereof. Preferably the cross-linking agent comprises $C_1$-$C_4$ tetra-alkoxy derivatives of silicon, more preferably the cross-linking agent comprises tetraethoxysilane.

Regarding Formula III, R is preferably hydrogen. Typical examples of the divalent linking group Q' include those described with respect to Formula I. Linking groups Q' for Formula III are favorably selected from the group consisting of alkylene (preferably containing 2 to 20, more preferably 2 to 10 carbon atoms), oxyalkylene (preferably containing 2 to 20 carbon atoms and 1 to 10 oxygen atoms), aminoalkylene (preferably containing 2 to 20 carbon atoms and 1 to 10 nitrogen atoms) and carbonyloxyalkylene (preferably containing 3 to 20 carbons atoms).

L in Formula IIIa represents a reactive functional group that may react by condensation or addition reactions or by free-radical polymerization reactions. Desirably L is selected from the group consisting of an amino group, an epoxy group, a mercaptan group, an anhydride group, vinyl ether group, vinyl ester group, allyl group, allyl ester group, vinyl ketone group, styrene group, vinyl amide group, acrylamide group, maleate group, fumarate group, acrylate group and methacrylate group.

Representative examples of favorable non-fluorinated silicon compounds in accordance with Formula IIIa for use in a cross-linking agent include 3-glycidoxy-propyltrimethoxysilane; 3-glycidoxypropyltriethoxysilane; 3-aminopropyl-trimethoxysilane; 3-aminopropyltriethoxysilane; bis(3-trimethoxysilylpropyl)amine; 3-aminopropyl tri (methoxyethoxyethoxy) silane; N (2-aminoethyl)-3-aminopropyltrimethoxysilane; bis(3-trimethoxysilylpropyl) ethylenediamine; 3-mercaptopropyltrimethoxysilane; 3-mercaptopropyltriethoxysilane; 3-trimethoxysilyl-propylmethacrylate; 3-triethoxysilypropylmethacrylate; bis(trimethoxysilyl) itaconate; allyltriethoxysilane; allyltrimetoxysilane; 3-(N-allylamino)propyltrimethoxysilane; vinyltrimethoxysilane; vinyltriethoxysilane; and mixtures thereof.

The amounts by weight of the multifunctional polyfluoropolyether silane to the non-fluorinated cross-linking agent can change from about 10:1 to about 1:100, preferably from about 1:1 to about 1:50 and most preferably from about 1:2 to about 1:20.

Generally the use of a cross-linking agent is not necessary for cross-linking of multifunctional polyfluoropolyether silane compounds described herein, however the use of a cross-linking agent may provide an economic benefit (e.g. allowing a reduction in the amount of relatively expensive fluorosilane to be applied) and/or facilitate attachment (e.g. covalent bonding) of polyfluoropolyether-containing coatings described herein. In particular for certain embodiments including a cross-linking agent comprising one or more compounds having at least one reactive functional group and at least one hydrolysable group per molecule, the use of such agents can advantageously facilitate and/or enhance attachment and covalent bonding of polyfluoropolyether-containing coatings as described herein onto a non-metal surface (e.g. a plastic surface) of a medicinal inhalation device or a component (e.g. onto components made of a plastic, such as a MDI actuator made of polyethylene or polypropylene or a metered dose valve component (e.g. a valve body or a valve stem) made of acetal, nylon, a polyester (e.g. PBT; TBT), a PEEK, a polycarbonate or a polyalkylene).

Coatings provided through the application of a composition comprising a multifunctional polyfluoropolyether silane and a cross-linking agent comprising a compound in accordance with Formula IIa, desirably contain entities in accordance with the Formula IIb:

$$Si(O-)_{4-g}(R^5)_g \qquad \text{IIb}$$

where $R^5$ represents a non-hydrolysable group (as described above), and g is 0, 1, 2 (preferably 0 or 1, more preferably 0). Desirably the at least one covalent bond shared with the surface of the medicinal inhalation device or the surface of a component of a medicinal inhalation device, as applicable, includes a bond to an oxygen atom in Si(O—)$_4$—g.

Similarly coatings provided through the application of a composition comprising a multifunctional polyfluoropolyether silane and a cross-linking agent comprising a compound in accordance with Formula IIIa, desirably contain entities in accordance with the Formula IIIb:

$$-L'-Q'C(R)_2Si(O-)_{3-g}-(R^5)_g \qquad \text{IIIb}$$

where $R^5$ represents a non-hydrolysable group (as described above), and g is 0, 1, 2 (preferably 0 or 1, more preferably 0); Q' represents an organic divalent linking group (as described above); each R is independently hydrogen or a $C_{1-4}$ alkyl group (preferably hydrogen) and L' represents a derivative of a reactive functional group (e.g. a derivative of a reactive functional group L described above resulting from a condensation reaction or an addition reaction or a free-radical polymerization reaction). Advantageously the at least one covalent bond shared with the surface of the medicinal inhalation device or the surface of a component of a medicinal inhalation device, as applicable, includes a bond to L'.

Compositions comprising a multifunctional polyfluoropolyether silane, including any one of the above described embodiments, can be applied to at least a portion of the surface of the medicinal inhalation device or the component thereof using a variety of coating methods. Such methods include but are not limited to spraying, dipping, spin coating, rolling, brushing, spreading and flow coating. Preferred methods for application include spraying and dipping. For certain embodiments the composition, in any one of its above described embodiments, is applied by dipping at least a portion of the substrate to be coated in said composition. Alternatively, for certain embodiments, the composition, in any one of its above described embodiments, is applied by spraying at least a portion of the substrate to be coated with said composition. For the preparation of a durable coating, sufficient water should be present to cause hydrolysis of the hydrolyzable groups described above e.g. so that condensation to form —O—Si groups takes place, and thereby curing takes place. The water can be present either in the treating composition or adsorbed to the substrate surface, for example. Typically, sufficient water is present for the preparation of a durable coating if the application is carried out at room temperature in an atmosphere containing water, for example, an atmosphere having a relative humidity of about 30% to about 80%.

Application is typically carried out by contacting the substrate with the treating composition, generally at room temperature (typically about 20° C. to about 25° C.). Alternatively treating composition can be applied to a substrate that is pre-heated at a temperature of for example between 60° C. and 150° C. Following application the treated substrate allow to dry and cure at ambient temperature (typically about 20° C. up to but not including 40° C.). Alternatively, as desired or needed, the treated substrate can be dried and cured at elevated temperatures (e.g. at 40° C. to 300° C.) and for a time sufficient to dry and cure. If desired or needed, the treating composition may further comprise a thermal initiator. Examples of suitable thermal initiators include, among others, organic peroxides in the form of diacyl peroxides, peroxydicarbonates, alkyl peresters, dialkyl peroxides, perketals, ketone peroxides and alkyl hydroperoxides. Specific examples of such thermal initiators are dibenzoyl peroxide, tert-butyl perbenzoate and azobisisobutyronitrile. Alternatively or in addition thereto, following application of the treating composition the treated substrate may be cured (again if desired or needed) by irradiation (e.g. means of UV-irradiators, etc.). Hereto the treating composition typically further comprises a photo-initiator, and curing is performed in a manner known per se, depending on the type and presence, respectively of the photo-initiator used in the treating composition. Photo-initiators for irradiation curing are commercially available and include e.g. benzophenone; photo-initiators available under the trade designation IRGACURE from Ciba-Geigy (e.g., IRGACURE 184 (1-hydroxy-cyclohexyl phenyl ketone) and IRGACURE 500 (1-hydroxy-cyclohexyl phenyl ketone, benzophenone); and photo-initiators available under the trade designation DARPCUR from Merck.

It is particularly advantageous for certain embodiments of methods described herein where the composition comprises a multifunctional polyfluoropolyether silane additionally includes a non-fluorinated cross-linking agent comprising one or more non-fluorinated compounds, one or more compounds having at least one reactive functional group as described herein, to perform a thermal curing step, or irradiation-induced curing step, or a two-fold curing (e.g. an irradiation-induced curing followed by a thermal curing or a thermal curing followed by a second thermal curing). The appropriate selection of curing depends on the particular compound(s) used in the cross-linking agent and the particular reactive functional group(s) of the compound(s). For example a substrate treated with such a composition including a compound having a reactive amino functional group (e.g., 3-aminopropyltrimethoxysilane; 3-aminopropyltriethoxysilane, bis (3-trimethoxysilylpropyl)amine; 3-aminopropyl tri(methoxyethoxyethoxy) silane; N (2-aminoethyl)-3-aminopropyltrimethoxysilane; and, bis(3-trimethoxysilylpropyl)ethylenediamine) are typically subjected to a thermal curing. A substrate treated with a composition including a compound having a reactive functional selected from the group consisting of an epoxy group, mercaptan group, anhydride group (e.g., 3-glycidoxy-propyltrimethoxysilane, 3-glycidoxypropyltriethoxysilane, 3-mercaptopropyl-trimethoxysilane, and 3-mercaptopropyltriethoxysilane) may be subjected to a thermal curing or an irradiation-induced curing (preferably a thermal curing). A substrate treated with a composition including a compound having a reactive functional group which react by free-radial polymerization (e.g., 3-trimethoxysilylpropylmethacrylate, 3-triethoxysilyl-propylmethacrylate, bis(trimethoxysilyl) itaconate, allyltriethoxysilane, allyltrimetoxysilane, 3-(N-allylamino)propyltrimethoxysilane, vinyltrimethoxysilane and vinyltriethoxysilane) are typically subjected to an irradiation-induced curing, but also may be, alternatively (and in some embodiments more favorably), subjected to a thermal curing. It will be appreciated that the respective treating composition may include, as desired or needed, an appropriate initiator for the particular type of curing, e.g. a photo-initiator and/or a thermal initiator. Suitable photo-initiator and thermal initiators are described above. Typically an initiator will be added in an amount between 0.1 and 2% by weight based on the weight of the compound(s) of the cross-linking agent.

For effective and efficient coating of components of medicinal inhalation devices, in particular complex-shaped components having restricted/constrained cavities or channels, for those favorable embodiments employing a composition comprising a cross-linking agent, the use of cross-linking agents that are cured under ambient temperatures and/or elevated temperatures are particularly advantageous.

A post-treatment process may include a rinsing step (e.g. before or after drying/curing, as desired or needed) to remove excess material, followed by a drying step.

Methods described herein may include a pre-treatment step prior to the step of applying to at least a portion of a surface of the medicinal inhalation device or to at least a portion of a surface of the component of a medicinal inhalation device, as applicable, a composition comprising a multifunctional polyfluoropolyether silane as described herein. Favorably the pre-treatment step comprises exposing said surface to an oxygen plasma, in particular an oxygen plasma under conditions of ion bombardment (i.e. generating an ion sheath and having the substrate to be coated located within the ion sheath during said oxygen plasma treatment). Alternatively and more favorably, the pre-treatment step comprises exposing said surface to a corona discharge. Such pre-treatments may desirably facilitate the provision of extensive bonding of the polyfluoropolyether-containing coating to the surface of the medicinal inhalation device or the surface of a component of the medicinal inhalation device, as applicable, and thus facilitate overall structural integrity of the coating over the lifetime of the device. Such pre-treatments are particularly advantageous, when coating plastic surfaces (e.g. components made of plastic, such as MDI valve components or actuators), more particularly when coating such plastic surfaces with compositions that do not include a cross-linking agent including a compound having a reactive functional group as described herein. Corona discharge treatment is particular advantageous in that it is highly effective and efficient in activating surfaces while at the same time allowing for quick, easy and cost-efficient pre-treatment on large scale.

In certain embodiments of methods described herein, the surface is aluminum or an aluminum alloy. For example, in methods applying to at least a portion of a surface of a component of a medicinal inhalation device a composition comprising a multifunctional polyfluoropolyether silane, the component may be made of aluminum or an aluminum alloy. Examples of such components include components of MDIs, such as canisters, ferrules, and metered dose valve components (such as valve bodies and valves stems). For such methods favorably such methods further comprise a step of anodizing said surface, where such step of anodizing is performed prior to the step of applying the composition and if applicable, such step of anodizing is performed prior to a pre-treatment step as described. Anodizing is beneficial in hardening the aluminum or aluminum alloy as well as removing or minimizing surface imperfections resulting from fabrication (such as deep drawing) and facilitating the naturally occurring oxide process, all of which further facilitate overall durability of the component as well as application efficiency of and subsequent structural integrity of the applied polyfluoropolyether-containing coating.

Methods described herein may further include a step of pre-washing said surface to clean and/or degrease the surface (e.g. to remove petroleum-based drawing oil typically used in deep-drawing metal components like MDI canisters or valve components). Such a pre-washing step may be performed with a solvent, in particular an organic solvent such as trichloroethylene, acetone or ethanol, or alternatively with an aqueous detergent solution followed by rinsing with water, and if applicable drying. Such a pre-washing step would typically be performed prior to the step of applying a composition comprising a multifunctional polyfluoropolyether silane as described herein. If applicable, such a pre-washing step may be performed prior to any pre-treatment step. Further and again if applicable, such a pre-washing step may be performed prior to any anodizing step.

It has been found advantageous to form a component (in particular a metal component) of a medicinal inhalation device (in particular to form by deep-drawing, machining, or impact extrusion) using an oil comprising a hydrofluoroether or a mixture of hydrofluoroethers. For such formed components it has been determined that a pre-washing step can generally be avoided, which is advantageous in processing/manufacturing efficient as well as cost-efficient. Favorably the hydrofluoroether is selected from the group consisting of methyl heptafluoropropylether; methyl nonafluorobutylether; ethyl nonafluorobutylether; 2-trifluoromethyl-3-ethoxydodecafluorohexane and mixtures thereof.

Methods described herein are desirably free of a step of pre-coating the surface of medicinal inhalation device or the surface of the component of the medicinal inhalation device, respectively, prior to applying the composition comprising a multifunctional polyfluoropolyether silane according to any embodiment described herein. Medicinal inhalation devices and components of such devices comprising a polyfluoropolyether-containing coating covalently bonded to at least a portion of a surface of the device or the component, respectively, as described herein are desirably free of an undercoating.

Besides the provision of medicinal inhalation devices and components thereof having desirable surface properties and structural integrity, methods of providing such medicinal inhalation devices and components as described herein are advantageous in their versatility and/or broad applicability to making various components of such medicinal inhalation devices, such components having significantly differing shapes and forms made of significantly differing materials. For example methods described herein can be advantageously used to provide a coating on at least a portion of the interior surface (preferably on the entire interior surface, more preferably the entire surface) of an MDI aerosol container, in particular a conventional MDI aerosol container made of aluminum or an aluminum alloy as well as MDI aerosol containers made of other metals, such as stainless steel. Methods described herein can also be advantageously used to provide a coating on at least a portion of a surface (preferably the entire surface) of a valve stem or a valve body, in particular a valve stem or a valve body made of a polymer such as PBT or acetal. This is advantageous for large scale manufacturing and coating as well as stream-lining of manufacturing processing, facilities and/or equipment for coating, while at the same time allowing freedom in regard to the selection of the base material of a component and in some instances expanding the possibilities of the base material for a component.

As detailed above, some polyfluoropolyether-containing coatings described herein are advantageously transparent or translucent (in particular those coatings have a thickness of 100 nm or less), and such coatings can be used to provide a transparent or translucent plastic MDI aerosol container which can be advantageous in that a patient can easily monitor the content of the container (i.e. whether it is empty and needs to be replaced).

Methods described herein can also be used to provide other medicinal inhalation devices including nebulizers, pump spray devices, nasal pumps, non-pressurized actuators or components of such devices. Accordingly medicinal inhalation devices or components described herein may also be nebulizers, pump spray devices, nasal pumps, non-pressurized actuators or components of such devices.

Methods described herein can also be used to provide other components used in medicinal inhalation such as breath-actuating devices, breath-coordinating devices, spacers, dose counters, or individual components of such devices, spacers and counters, respectively. Accordingly components described herein may also be breath-actuating devices, breath-coordinating devices, spacers, dose counters, or individual components of such devices, spacers, counters, respectively. In regard to provision of a component or components of dose counters of medicinal inhalation devices, due to desirable surface properties and structural integrity (in particular durability and resistance to wear) of coatings described herein, the provision of such a coating on a component or components (in particular movable component(s) and/or component(s) in contact with a movable component) of a dose counter provides dry lubricity facilitating smooth operation of the dose counter.

Objects and advantages of this invention are further illustrated by the following examples, but the particular materials and amounts thereof recited in these examples, as well as other conditions and details, should not be construed to unduly limit this invention.

EXAMPLES

Preparation of $(CH_3O)_3Si(CH_2)_3N(H)C(O)CF_2O(CF_2CF_2O)_{9-10}(CF_2O)_{9-10}CF_2C(O)N(H)(CH_2)_3Si(OCH_3)_3$ $CH_3OC(O)CF_2O(CF_2CF_2O)_{9-10}(CF_2O)_{9-10}CF_2C(O)OCH_3$ (a perfluoropolyether diester obtained from Solvay Solexis, Houston, Tex., available under the trade designation "FOMBLIN ZDEAL") (50 grams (g)) was added to an oven-dried 100-mL round bottom flask under a nitrogen atmosphere and stirred rapidly at room temperature using a magnetic stirrer. 3-Aminopropyltrimethoxysilane (9.1 g) (obtained from GE Silicones, Wilton, Conn., available under the trade designation "SILQUEST A-1110") was added to the flask in one portion. Initially the mixture was two-phase, and as the reagents mixed the mixture became cloudy. A reaction exotherm to a temperature of about 50° C. was observed, the reaction was continued for 2 hours at 60° C. and then the reaction gradually cooled to room temperature and became a slightly hazy light yellow liquid. The reaction was monitored by gas chromatography (GC) to observe excess 3-aminopropyltrimethoxysilane and Fourier transform infrared spectroscopy (FTIR) to observe unreacted ester functional groups and was found to be complete within 90 minutes after the addition of the 3-aminopropyltrimethoxysilane. The reaction product was stirred rapidly, and the pressure in the flask was reduced to 1 mmHg (133 Pa) gradually to minimize bumping. Methanol by-product was distilled from the flask over a period of two hours, and 57.5 g of

was recovered from the flask. (Average molecular weight is about 2400 and fraction of silane with a polyfluoropolyether segment having a weight average MW lower than 750 is zero).

Exemplary Silane Treatment Methods

The following are exemplary silane treatment methods:

Method A:
Place a solution (3 liters (L)) of 0.1% (w/w) $(CH_3O)_3Si(CH_2)_3N(H)C(O)CF_2(CF_2CF_2O)_{9-10}(CF_2O)_{9-10}CF_2C(O)N(H)(CH_2)_3Si(OCH_3)_3$ in HFE-7100 fluid (available from 3M Company, St. Paul, Minn. under the trade designation "NOVEC HFE-7100") in a 4-L beaker at room temperature, and place beaker in a dip coater. Fix component to be coated vertically above the solution, introduce component into the solution at a controlled rate of 15 millimeters per second (submerging the component entirely in the solution) and hold in place for at least five seconds. Subsequently withdrawn component from the solution at a controlled rate of 15 millimeters (mm) per second and allow to drain. After draining, place component in an aluminum pan and then place the pan in an oven at 120° C. for 30 minutes. After removing from oven, allow component to stand at least 24 hours.

Method B:
The method is the same as Method A with the exception of placing a solution (3 liters (L)) of 0.1% (w/w) $(CH_3O)_3Si(CH_2)_3N(H)C(O)CF_2(CF_2CF_2O)_{9-10}(CF_2O)_{9-10}CF_2C(O)N(H)(CH_2)_3Si(OCH_3)_3$ and 0.6% (w/w) tetraethoxysilane and 1% (w/w) acetic acid in HFE-7200 fluid (available from 3M Company, St. Paul, Minn. under the trade designation "NOVEC HFE-7200") in a 4-L beaker Method C:
The method is the same as Method A with the exception of placing a solution (3 liters (L)) of 0.1% (w/w) $(CH_3O)_3Si(CH_2)_3N(H)C(O)CF_2(CF_2CF_2O)_{9-10}(CF_2O)_{9-10}CF_2C(O)N(H)(CH_2)_3Si(OCH_3)_3$; 0.6% (w/w) 3-glycidoxypropyltrimethoxysilane and 1% (w/w) acetic acid in HFE-7200 fluid in a 4-L beaker.

Thickness of a coating resulting from following any one of Methods A to C is in the range of about 50 to about 80 nanometers.

Examples 1 and 2

Standard deep drawn aluminum MDI containers having a nominal volume of 10 milliliters are washed with trichloroethylene and coated in accordance with Method A (Example 1) and Method B (Example 2), respectively. Containers are fitted with metered dose valves of the type marketed under the trade designation SPRAYMISER (3M Company, St. Paul, Minn., USA) having a 50 mcl metering chamber and then a formulation consisting of 1.97 mg/ml albuterol sulfate (having a majority of particles in the range of 1 to 3 microns) and HFA 134a is pressure-filled into the canisters.

Examples 3 and 4

Standard deep drawn aluminum MDI containers having a volume of 10 millimeters are washed with trichloroethylene, anodized and coated in accordance with Method A (Example 3) and Method B (Example 4), respectively. Containers are fitted with metered dose valves of the type marketed under the trade designation SPRAYMISER (3M Company, St. Paul, Minn., USA) having a 50 mcl metering chamber and then a formulation consisting of 1.97 mg/ml albuterol sulfate (having a majority of particles in the range of 1 to 3 microns) and HFA 134a is pressure-filled into the canisters.

Examples 5 and 6

Standard deep drawn aluminum MDI containers having a volume of 10 millimeters are washed with trichloroethylene, exposed to a corona discharge and then are coated in accordance with Method A (Example 5) and Method B (Example 6), respectively. Containers are fitted with metered dose valves of the type marketed under the trade designation SPRAYMISER (3M Company, St. Paul, Minn., USA) having a 50 mcl metering chamber and then a formulation consisting of 1.97 mg/ml albuterol sulfate (having a majority of particles in the range of 1 to 3 microns) and HFA 134a is pressure-filled into the canisters.

Examples 7 and 8

Aluminum MDI containers having a volume of 10 millimeters are deep drawn using methyl nonafluorobutylether as a drawing oil and after forming are coated in accordance with Method A (Example 7) and Method B (Example 8), respectively. Containers are fitted with metered dose valves of the type marketed under the trade designation SPRAYMISER (3M Company, St. Paul, Minn., USA) having a 50 mcl metering chamber and then a formulation consisting of 1.97 mg/ml albuterol sulfate (having a majority of particles in the range of 1 to 3 microns) and HFA 134a is pressure-filled into the canisters.

Examples 9 and 10

Compression springs, primary valve bodies and machined valve stems, all of stainless steel, for metered dose valves of the type similar to that shown in FIG. 1 having a 63 mcl metering chamber are washed with trichloroethylene and coated in accordance with Method A (Example 9) and Method B (Example 10), respectively, and then respective valves are constructed and crimped onto standard aluminum MDI containers containing a chilled formulation consisting of 1.97 mg/ml albuterol sulfate (having a majority of particles in the range of 1 to 3 microns) and HFA 134a (within a dehumidified glovebox).

Examples 11 and 12

Standard deep drawn aluminum MDI containers having a nominal volume of 12.5 milliliters are washed with trichloroethylene and coated in accordance with Method A. Compression springs, primary valve bodies and machined valve stems, all of aluminum, for metered dose valves of the type similar to that shown in FIG. 1 having a 63 mcl metering chamber are washed with trichloroethylene and coated in accordance with Method A (Example 11) and Method B (Example 12), respectively, and then respective valves are constructed and crimped onto the containers. A formulation consisting of 1.97 mg/ml albuterol sulfate (having a majority of particles in the range of 1 to 3 microns) and HFA 134a is pressure-filled into the canisters.

Examples 13 and 14

Acetal valve stems for valves of the type marketed under the trade designation BK357 (Bespak plc, Bergen Way, Kings Lynn Norfolk PE 30 2JJ) having a 50 mcl metering chamber are coated in accordance with Method A (Example 13) and Method B (Example 14), respectively, and then the respective valves are constructed and crimped onto standard deep drawn aluminum MDI containers. A formulation consisting of 1.97 mg/ml albuterol sulfate (having a majority of particles in the range of 1 to 3 microns) and HFA 134a is pressure-filled into the canisters.

Examples 15 and 16

PBT primary valve bodies for valves of the type marketed under the trade designation BK357 (Bespak plc, Bergen Way, Kings Lynn Norfolk PE 30 2JJ) having a 50 mcl metering chamber are exposed to a corona discharge and coated in accordance with Method A (Example 15) and Method B (Example 16), respectively, and then respective valves are constructed and crimped onto standard deep drawn aluminum MDI containers. A formulation consisting of 1.97 mg/ml albuterol sulfate (having a majority of particles in the range of 1 to 3 microns) and HFA 134a is pressure-filled into the canisters.

Example 17

PBT primary valve bodies for valves of the type marketed under the trade designation BK357 (Bespak plc, Bergen Way, Kings Lynn Norfolk PE 30 2JJ) having a 50 mcl metering chamber are coated in accordance with Method C, and then respective valves are constructed and crimped onto standard deep drawn aluminum MDI containers. A formulation consisting of 1.97 mg/ml albuterol sulfate (having a majority of particles in the range of 1 to 3 microns) and HFA 134a is pressure-filled into the canisters.

Example 18

Acetal valve stems and PBT primary valve bodies for valves of the type marketed under the trade designation BK357 (Bespak plc, Bergen Way, Kings Lynn Norfolk PE 30 2JJ) having a 50 mcl metering chamber are coated in accordance with Method C, and then respective valves are constructed and crimped onto standard deep drawn aluminum MDI containers. A formulation consisting of 1.97 mg/ml albuterol sulfate (having a majority of particles in the range of 1 to 3 microns) and HFA 134a is pressure-filled into the canisters.

Example 19 and 20

Polypropylene actuators of the type similar to that shown in FIG. 1 are exposed to a corona discharge and coated in accordance with Method A (Example 19) and Method B (Example 20), respectively.

Example 21

Polypropylene actuators of the type similar to that shown in FIG. 1 are coated in accordance with Method C.

The invention claimed is:

1. A method of making a medicinal inhalation device or a component of a medicinal inhalation device comprising a step of: applying to at least a portion of a surface of the device or the component, respectively, a composition comprising a multifunctional polyfluoropolyether silane, wherein the polyfluoropolyether segment of the polyfluoropolyether silane is not linked to the functional silane groups via a functionality that includes nitrogen-silicon bond or a sulfur-silicon bond.

2. A method according to claim 1, wherein the polyfluoropolyether segment of the polyfluoropolyether silane is linked to the functional silane groups via a functionality that includes a carbon-silicon bond.

3. A method according to claim 2, wherein the polyfluoropolyether segment of the polyfluoropolyether silane is linked to the functional silane groups via a $-C(R)_2-Si$ functionality where R is independently hydrogen or a $C_{1-4}$ alkyl group.

4. A method according to claim 3, wherein the polyfluoropolyether segment of the polyfluoropolyether silane is linked to the functional silane groups via a $-(CR_2)_k-C(R)_2-Si$ functionality where k is at least 2 and where R is independently hydrogen or a $C_{1-4}$ alkyl group.

5. A method according to claim 1, wherein the polyfluoropolyether segment of the polyfluoropolyether is a perfluorinated polyfluoropolyether segment.

6. A method according to claim 5, wherein in the repeating units of the perfluorinated polyfluoropolyether segment the number of carbon atoms in sequence is at most 6, in particular at most 4, more particularly at most 3, and most particularly at most 2.

7. A method according to claim 1, wherein the multifunctional polyfluoropolyether silane is a difunctional polyfluoropolyether silane.

8. A method according to claim 1, wherein the weight average molecular weight of the polyfluoropolyether segment is about 1000 or higher, in particular about 1800 or higher.

9. A method according to claim 1 or 8, wherein the weight average molecular weight of the polyfluoropolyether segment is about 6000 or less, in particular about 4000 or less.

10. A method according to claim 1, wherein the composition is applied to said surface, such that polyfluoropolyether-containing coating provided on said surface has a thickness of at most about 300 nm.

11. A method according to claim 1 or 10, wherein the composition is applied to said surface, such that polyfluoropolyether-containing coating provided on said surface has a thickness of at least about 20 nm.

12. A medicinal inhalation device or a component of a medicinal inhalation device made according to claim 1.

13. A medicinal inhalation device or a component of a medicinal inhalation device comprising a polyfluoropolyether-containing coating bonded to at least a portion of a surface of the device or the component, respectively, said polyfluorpolyether-containing coating comprising a plurality of cross-linked, multifunctional polyfluoropolyether-silane entities and said polyfluorpolyether-containing coating sharing at least one covalent bond with said surface, wherein the polyfluoropolyether segment of the polyfluoropolyether silane entities is not linked to the functional silane groups via a functionality that includes nitrogen-silicon bond or a sulfur-silicon bond.

14. A device or a component according to claim 12 or 13, where said medicinal inhalation device is a metered dose inhaler or a dry powder inhaler.

* * * * *

UNITED STATES PATENT AND TRADEMARK OFFICE
CERTIFICATE OF CORRECTION

| | | |
|---|---|---|
| PATENT NO. | : 8,616,201 B2 | Page 1 of 1 |
| APPLICATION NO. | : 12/741497 | |
| DATED | : December 31, 2013 | |
| INVENTOR(S) | : Philip A. Jinks and Rudolf J. Dams | |

It is certified that error appears in the above-identified patent and that said Letters Patent is hereby corrected as shown below:

IN THE SPECIFICATION:

Column 5,
Line 9, "$CH_2\text{-}O\text{-}(CH_2)_2$" should read --$CH_2O(CH_2)_2$--.

Column 6,
Line 18, "Formula IIa," should read --Formula IIIa,--.
Line 56, "his (3-trimethoxysilylpropyl)amine" should read
    --bis(3-trimethoxysilylpropyl)amine--.
Line 58, "his (3-trimethoxysilylpropyl)" should read
    --bis(3-trimethoxysilylpropyl)--.
Line 61-62, "his (3-trimethoxysilyl)" should read
    --bis(3-trimethoxysilyl)--.

Column 10,
Line 44, "$CH_2\text{-}O\text{-}(CH_2)_2$" should read --$CH_2O(CH_2)_2$--.

Column 21,
Line 47-48, "$CH_2\text{-}O\text{-}(CH_2)_2$" should read --$CH_2O(CH_2)_2$--.

Column 26,
Line 58, "bis (3-trimethoxysilylpropyl)amine;" should read
    --bis(3-trimethoxysilylpropyl)amine;--.

Signed and Sealed this
Second Day of December, 2014

Michelle K. Lee
*Deputy Director of the United States Patent and Trademark Office*